(12) United States Patent
Altshuler et al.

(10) Patent No.: US 7,220,254 B2
(45) Date of Patent: May 22, 2007

(54) DERMATOLOGICAL TREATMENT WITH VISUALIZATION

(75) Inventors: Gregory B. Altshuler, Wilmington, MA (US); Liam O'Shea, Medford, MA (US); Oldrich M. Laznicka, Jr., Wellesley, MA (US)

(73) Assignee: Palomar Medical Technologies, Inc., Burlington, MA (US)

( * ) Notice: Subject to any disclaimer, the term of this patent is extended or adjusted under 35 U.S.C. 154(b) by 0 days.

(21) Appl. No.: 11/028,481

(22) Filed: Dec. 31, 2004

(65) Prior Publication Data

US 2005/0154382 A1 Jul. 14, 2005

Related U.S. Application Data

(60) Provisional application No. 60/534,060, filed on Dec. 31, 2003.

(51) Int. Cl.
*A61N 5/01* (2006.01)
*A61N 5/06* (2006.01)

(52) U.S. Cl. .......................... 606/9; 128/898; 606/13; 607/88

(58) Field of Classification Search ............... 128/898; 606/9; 607/88–94
See application file for complete search history.

(56) References Cited

U.S. PATENT DOCUMENTS

| 1,706,161 A | 3/1929 | Hollnagel |
|---|---|---|
| 2,472,385 A | 6/1949 | Rollman |
| 3,327,712 A | 6/1967 | Kaufman et al. |
| 3,486,070 A | 12/1969 | Engel |
| 3,527,932 A | 9/1970 | Thomas |
| 3,538,919 A | 11/1970 | Meyer |
| 3,622,743 A | 11/1971 | Muncheryan |
| 3,693,623 A | 9/1972 | Harte et al. |
| 3,818,914 A | 6/1974 | Bender |
| 3,834,391 A | 9/1974 | Block |
| 3,846,811 A | 11/1974 | Nakamura et al. |

(Continued)

FOREIGN PATENT DOCUMENTS

AU          1851583         3/1984

(Continued)

OTHER PUBLICATIONS

G.B. Altshuler et al., "Acoustic response of hard dental tissues to pulsed laser action," SPIE, vol. 2080, Dental Application of Lasers, pp. 97-103, 1993.

(Continued)

*Primary Examiner*—Henry M. Johnson, III
(74) *Attorney, Agent, or Firm*—Thomas J. Engellenner; Reza Mollaaghababa; Nutter McClennen & Fish LLP

(57) ABSTRACT

The present invention provides a handheld dermatological device for visualizing a skin treatment region prior to, during, or after therapeutic treatment with therapeutic energy. An apparatus according to the teachings of the invention can include an image capture device and a display device mounted to the apparatus and electrically coupled to the image capture device. The display device is capable of displaying images of the treatment area captured by the image capture device. The apparatus can further include a head capable of transmitting therapeutic energy to a treatment area, which can be precisely aligned by the user to a desired portion of the treatment area through the use of the display device. In some embodiments, the apparatus can include one or more illumination sources for illuminating a skin target region, and shield for shielding the image capture device from direct reflection of the illuminating radiation from a selected skin surface portion.

18 Claims, 24 Drawing Sheets

U.S. PATENT DOCUMENTS

| | | |
|---|---|---|
| 3,857,015 A | 12/1974 | Clark et al. |
| 3,900,034 A | 8/1975 | Katz |
| 4,233,493 A | 11/1980 | Nath |
| 4,273,109 A | 6/1981 | Enderby |
| 4,275,335 A | 6/1981 | Ishida |
| 4,316,467 A | 2/1982 | Muckerheide |
| 4,388,924 A | 6/1983 | Weissman et al. |
| 4,456,872 A | 6/1984 | Froeschle |
| 4,461,294 A | 7/1984 | Baron |
| 4,524,289 A | 6/1985 | Hammond et al. |
| 4,539,987 A | 9/1985 | Nath et al. |
| 4,591,762 A | 5/1986 | Nakamura |
| 4,608,978 A | 9/1986 | Rohr |
| 4,617,926 A | 10/1986 | Sutton |
| 4,677,347 A | 6/1987 | Nakamura |
| 4,695,697 A | 9/1987 | Kosa |
| 4,718,416 A | 1/1988 | Nanaumi |
| 4,733,660 A | 3/1988 | Itzkan |
| 4,745,909 A | 5/1988 | Pelton et al. |
| 4,747,660 A | 5/1988 | Nishioka et al. |
| 4,749,913 A | 6/1988 | Stuermer et al. |
| 4,819,669 A | 4/1989 | Politzer |
| 4,832,024 A | 5/1989 | Boussignac et al. |
| 4,860,172 A | 8/1989 | Schlager et al. |
| 4,860,744 A | 8/1989 | Johnson et al. |
| 4,884,560 A | 12/1989 | Kuracina |
| 4,917,084 A | 4/1990 | Sinofsky |
| 4,926,227 A | 5/1990 | Jensen |
| 4,928,038 A | 5/1990 | Nerone |
| 4,945,239 A | 7/1990 | Wist et al. |
| 5,000,752 A | 3/1991 | Hoskin et al. |
| 5,057,104 A | 10/1991 | Chess |
| 5,059,192 A | 10/1991 | Zaias |
| 5,065,515 A | 11/1991 | Iderosa |
| 5,071,417 A | 12/1991 | Sinofsky |
| 5,108,388 A | 4/1992 | Trokel |
| 5,127,395 A | 7/1992 | Bontemps |
| 5,137,530 A | 8/1992 | Sand |
| 5,140,984 A | 8/1992 | Dew et al. |
| 5,178,617 A | 1/1993 | Kuizenga et al. |
| 5,182,557 A | 1/1993 | Lang |
| 5,182,857 A | 2/1993 | Simon |
| 5,196,004 A | 3/1993 | Sinofsky |
| 5,207,671 A | 5/1993 | Franken et al. |
| 5,225,926 A | 7/1993 | Cuomo et al. |
| 5,226,907 A | 7/1993 | Tankovich |
| 5,267,399 A | 12/1993 | Johnston |
| 5,282,797 A | 2/1994 | Chess |
| 5,300,097 A | 4/1994 | Lerner et al. |
| 5,304,170 A | 4/1994 | Green |
| 5,306,274 A | 4/1994 | Long |
| 5,320,618 A | 6/1994 | Gustafsson |
| 5,334,191 A | 8/1994 | Poppas et al. |
| 5,334,193 A | 8/1994 | Nardella |
| 5,344,418 A | 9/1994 | Ghaffari |
| 5,344,434 A | 9/1994 | Talmore |
| 5,348,551 A | 9/1994 | Spears et al. |
| 5,350,376 A | 9/1994 | Brown |
| 5,380,317 A | 1/1995 | Everett et al. |
| 5,403,306 A | 4/1995 | Edwards et al. |
| 5,405,368 A | 4/1995 | Eckhouse |
| 5,415,654 A | 5/1995 | Daikuzono |
| 5,425,728 A | 6/1995 | Tankovich |
| 5,458,140 A | 10/1995 | Eppstein et al. |
| 5,474,549 A | 12/1995 | Ortiz et al. |
| 5,486,172 A | 1/1996 | Chess |
| 5,505,726 A | 4/1996 | Meserol |
| 5,505,727 A | 4/1996 | Keller |
| 5,519,534 A | 5/1996 | Smith |
| 5,522,813 A | 6/1996 | Trelles |
| 5,531,739 A | 7/1996 | Trelles |
| 5,531,740 A | 7/1996 | Black |
| 5,549,660 A | 8/1996 | Mendes et al. |
| 5,558,667 A | 9/1996 | Yarborough et al. |
| 5,578,866 A | 11/1996 | DePoorter et al. |
| 5,595,568 A | 1/1997 | Anderson et al. |
| 5,616,140 A | 4/1997 | Prescott |
| 5,620,478 A | 4/1997 | Eckhouse |
| 5,626,631 A | 5/1997 | Eckhouse |
| 5,630,811 A | 5/1997 | Miller |
| 5,649,972 A | 7/1997 | Hochstein |
| 5,653,706 A * | 8/1997 | Zavislan et al. ............ 606/9 |
| 5,655,547 A | 8/1997 | Karni |
| 5,658,323 A | 8/1997 | Miller |
| 5,660,836 A | 8/1997 | Knowlton |
| 5,662,643 A | 9/1997 | Kung et al. |
| 5,662,644 A | 9/1997 | Swor |
| 5,683,380 A | 11/1997 | Eckhouse et al. |
| 5,698,866 A | 12/1997 | Doiron et al. |
| 5,707,403 A | 1/1998 | Grove et al. |
| 5,720,772 A | 2/1998 | Eckhouse |
| 5,722,397 A | 3/1998 | Eppstein |
| 5,735,844 A | 4/1998 | Anderson et al. |
| 5,742,392 A | 4/1998 | Anderson et al. |
| 5,743,901 A | 4/1998 | Grove et al. |
| 5,755,751 A | 5/1998 | Eckhouse |
| 5,759,200 A | 6/1998 | Azar |
| 5,769,076 A | 6/1998 | Mackawa et al. |
| 5,782,249 A | 7/1998 | Weber et al. |
| 5,810,801 A | 9/1998 | Anderson et al. |
| 5,814,008 A | 9/1998 | Chen et al. |
| 5,814,040 A | 9/1998 | Nelson et al. |
| 5,814,041 A | 9/1998 | Anderson et al. |
| 5,817,089 A | 10/1998 | Tankovich et al. |
| 5,820,625 A | 10/1998 | Izawa et al. |
| 5,820,626 A | 10/1998 | Baumgardner |
| 5,824,023 A | 10/1998 | Anderson |
| 5,828,803 A | 10/1998 | Eckhouse |
| 5,830,208 A | 11/1998 | Muller |
| 5,836,877 A | 11/1998 | Zavislan |
| 5,836,999 A | 11/1998 | Eckhouse et al. |
| 5,840,048 A | 11/1998 | Cheng |
| 5,849,029 A | 12/1998 | Eckhouse et al. |
| 5,851,181 A | 12/1998 | Talmor |
| 5,853,407 A | 12/1998 | Miller |
| 5,860,967 A | 1/1999 | Zavislan et al. |
| 5,868,731 A | 2/1999 | Budnik et al. |
| 5,883,471 A | 3/1999 | Rodman et al. |
| 5,885,211 A | 3/1999 | Eppstein et al. |
| 5,885,273 A | 3/1999 | Eckhouse et al. |
| 5,885,274 A | 3/1999 | Fullmer et al. |
| 5,891,063 A | 4/1999 | Vigil |
| 5,893,828 A * | 4/1999 | Uram ..................... 600/108 |
| 5,913,883 A | 6/1999 | Alexander et al. |
| 5,920,374 A | 7/1999 | Vaphiades et al. |
| 5,944,748 A | 8/1999 | Mager et al. |
| 5,948,011 A | 9/1999 | Knowlton |
| 5,949,222 A | 9/1999 | Buono |
| 5,954,710 A | 9/1999 | Paolini et al. |
| 5,964,749 A | 10/1999 | Eckhouse et al. |
| 5,968,033 A | 10/1999 | Fuller |
| 5,968,034 A | 10/1999 | Fullmer et al. |
| 5,977,723 A | 11/1999 | Yoon |
| 6,015,404 A | 1/2000 | Altshuler et al. |
| 6,022,316 A | 2/2000 | Eppstein et al. |
| 6,026,828 A | 2/2000 | Altshuler |
| 6,027,495 A | 2/2000 | Miller |
| 6,030,399 A | 2/2000 | Ignotz et al. |
| 6,032,071 A | 2/2000 | Binder |
| RE36,634 E | 3/2000 | Ghaffari |
| 6,050,990 A | 4/2000 | Tankovich et al. |
| D424,197 S | 5/2000 | Sydlowski et al. |
| 6,056,738 A | 5/2000 | Marchitto et al. |
| 6,059,820 A | 5/2000 | Baronov |

| | | | | | | |
|---|---|---|---|---|---|---|
| 6,074,382 | A | 6/2000 | Asah et al. | 6,790,205 B1 | 9/2004 | Yamazaki et al. |
| 6,080,146 | A | 6/2000 | Altshuler et al. | 6,801,595 B2 * | 10/2004 | Grodzins et al. ............. 378/45 |
| 6,086,580 | A | 7/2000 | Mordon et al. | 6,808,532 B2 | 10/2004 | Andersen et al. |
| 6,096,029 | A | 8/2000 | O'Donnell, Jr. | RE38,670 E | 12/2004 | Asah et al. |
| 6,096,209 | A | 8/2000 | O'Brien et al. | 6,878,144 B2 | 4/2005 | Altshuler et al. |
| 6,104,959 | A | 8/2000 | Spertell | 6,888,319 B2 | 5/2005 | Inochkin et al. |
| 6,117,129 | A | 9/2000 | Mukai | 7,001,413 B2 * | 2/2006 | Butler .......................... 607/88 |
| 6,120,497 | A | 9/2000 | Anderson | 7,006,223 B2 * | 2/2006 | Mullani ..................... 356/369 |
| 6,142,650 | A * | 11/2000 | Brown et al. ................ 362/259 | 2001/0041886 A1 | 11/2001 | Durkin et al. |
| 6,142,939 | A | 11/2000 | Eppstein et al. | 2002/0005475 A1 | 1/2002 | Zenzie |
| 6,149,644 | A | 11/2000 | Xie | 2002/0026225 A1 | 2/2002 | Segal |
| 6,162,211 | A | 12/2000 | Tankovich et al. | 2002/0091377 A1 | 7/2002 | Anderson |
| 6,162,212 | A | 12/2000 | Kreindel et al. | 2002/0123745 A1 | 9/2002 | Svaasand et al. |
| 6,173,202 | B1 | 1/2001 | Eppstein et al. | 2002/0128635 A1 | 9/2002 | Altshuler et al. |
| 6,174,325 | B1 | 1/2001 | Eckhouse | 2002/0161357 A1 | 10/2002 | Anderson |
| 6,183,434 | B1 | 2/2001 | Eppstein | 2002/0173780 A1 | 11/2002 | Altshuler et al. |
| 6,183,500 | B1 | 2/2001 | Kohler | 2003/0023235 A1 * | 1/2003 | Cense et al. .................... 606/9 |
| 6,183,773 | B1 | 2/2001 | Anderson | 2003/0023283 A1 | 1/2003 | McDaniel |
| 6,197,020 | B1 | 3/2001 | O'Donnell | 2003/0032900 A1 | 2/2003 | Ella |
| 6,210,425 | B1 | 4/2001 | Chen | 2003/0032950 A1 | 2/2003 | Altshuler et al. |
| 6,214,034 | B1 | 4/2001 | Azar | 2003/0036680 A1 | 2/2003 | Black |
| 6,229,831 | B1 | 5/2001 | Nightingale et al. | 2003/0055414 A1 | 3/2003 | Altshuler et al. |
| 6,235,016 | B1 | 5/2001 | Stewart | 2003/0057875 A1 | 3/2003 | Inochkin et al. |
| 6,236,891 | B1 | 5/2001 | Ingle et al. | 2003/0065314 A1 | 4/2003 | Altshuler et al. |
| 6,263,233 | B1 | 7/2001 | Zavislan et al. | 2003/0100936 A1 | 5/2003 | Altshuler et al. |
| 6,264,649 | B1 | 7/2001 | Whitcroft et al. | 2003/0109787 A1 | 6/2003 | Black |
| 6,267,780 | B1 | 7/2001 | Streeter | 2003/0109860 A1 | 6/2003 | Black |
| 6,273,884 | B1 | 8/2001 | Altshuler et al. | 2003/0129154 A1 | 7/2003 | McDaniel |
| 6,273,885 | B1 | 8/2001 | Koop et al. | 2003/0195494 A1 | 10/2003 | Altshuler et al. |
| 6,280,438 | B1 | 8/2001 | Eckhouse et al. | 2003/0199859 A1 | 10/2003 | Altshuler et al. |
| 6,290,713 | B1 | 9/2001 | Russell | 2003/0232303 A1 | 12/2003 | Black |
| 6,306,130 | B1 | 10/2001 | Anderson et al. | 2004/0006332 A1 | 1/2004 | Black |
| 6,306,160 | B1 | 10/2001 | Nidetzky | 2004/0010298 A1 | 1/2004 | Altshuler et al. |
| 6,319,274 | B1 | 11/2001 | Shadduck | 2004/0015156 A1 | 1/2004 | Vasily |
| 6,340,495 | B1 | 1/2002 | Sumian et al. | 2004/0024388 A1 | 2/2004 | Altshuler |
| 6,350,276 | B1 | 2/2002 | Knowlton | 2004/0030326 A1 | 2/2004 | Altshuler et al. |
| 6,354,370 | B1 | 3/2002 | Miller et al. | 2004/0034319 A1 | 2/2004 | Anderson et al. |
| 6,358,272 | B1 | 3/2002 | Wilden | 2004/0034341 A1 | 2/2004 | Altshuler et al. |
| 6,383,177 | B1 | 5/2002 | Balle-Petersen et al. | 2004/0073079 A1 | 4/2004 | Altshuler et al. |
| 6,387,089 | B1 | 5/2002 | Kreindel et al. | 2004/0082940 A1 | 4/2004 | Black et al. |
| 6,402,739 | B1 | 6/2002 | Neev | 2004/0085026 A1 | 5/2004 | Inochkin et al. |
| 6,406,474 | B1 | 6/2002 | Neuberger et al. | 2004/0093042 A1 | 5/2004 | Altshuler et al. |
| 6,424,852 | B1 | 7/2002 | Zavislan | 2004/0133251 A1 | 7/2004 | Altshuler et al. |
| 6,436,094 | B1 | 8/2002 | Reuter | 2004/0147984 A1 | 7/2004 | Altshuler et al. |
| 6,471,712 | B2 | 10/2002 | Burres | 2004/0162549 A1 | 8/2004 | Altshuler |
| 6,475,211 | B2 | 11/2002 | Chess et al. | 2004/0162596 A1 | 8/2004 | Altshuler et al. |
| 6,508,785 | B1 | 1/2003 | Eppstein | 2004/0191729 A1 | 9/2004 | Altshuler et al. |
| 6,508,813 | B1 | 1/2003 | Altshuler | 2004/0193234 A1 * | 9/2004 | Butler .......................... 607/88 |
| 6,511,475 | B1 | 1/2003 | Altshuler et al. | 2004/0193235 A1 | 9/2004 | Altshuler et al. |
| 6,514,242 | B1 | 2/2003 | Vasily et al. | 2004/0193236 A1 | 9/2004 | Altshuler et al. |
| 6,514,243 | B1 | 2/2003 | Eckhouse et al. | 2004/0199227 A1 | 10/2004 | Altshuler et al. |
| 6,517,532 | B1 | 2/2003 | Altshuler et al. | 2004/0204745 A1 | 10/2004 | Altshuler et al. |
| 6,530,915 | B1 | 3/2003 | Eppstein et al. | 2004/0210276 A1 | 10/2004 | Altshuler et al. |
| 6,537,270 | B1 | 3/2003 | Elbrecht et al. | 2004/0214132 A1 | 10/2004 | Altshuler |
| 6,558,372 | B1 | 5/2003 | Altshuler | 2004/0225339 A1 | 11/2004 | Yaroslavsky et al. |
| 6,602,245 | B1 | 8/2003 | Thiberg | 2004/0230258 A1 | 11/2004 | Altshuler et al. |
| 6,605,080 | B1 | 8/2003 | Altshuler et al. | 2005/0038418 A1 | 2/2005 | Altshuler et al. |
| 6,629,971 | B2 | 10/2003 | McDaniel | 2005/0049582 A1 | 3/2005 | DeBenedictis et al. |
| 6,632,219 | B1 | 10/2003 | Baranov et al. | 2005/0049658 A1 | 3/2005 | Connors et al. |
| 6,641,578 | B2 * | 11/2003 | Mukai ............ 606/9 | 2005/0107849 A1 | 5/2005 | Altshuler et al. |
| 6,648,904 | B2 | 11/2003 | Altshuler et al. | | | |
| 6,653,618 | B2 | 11/2003 | Zenzie | | | |
| 6,660,000 | B2 | 12/2003 | Neuberger et al. | | FOREIGN PATENT DOCUMENTS | |
| 6,663,620 | B2 | 12/2003 | Altshuler et al. | EP | 0142671 | 5/1985 |
| 6,663,659 | B2 | 12/2003 | McDaniel | EP | 0565331 | 10/1993 |
| 6,676,654 | B1 | 1/2004 | Balle-Petersen et al. | EP | 0598984 | 6/1994 |
| 6,679,837 | B2 | 1/2004 | Daikuzono | EP | 0724894 | 8/1996 |
| 6,685,699 | B1 | 2/2004 | Eppstein et al. | EP | 0726083 | 8/1996 |
| 6,689,124 | B1 | 2/2004 | Thiberg | EP | 0736308 | 10/1996 |
| 6,706,035 | B2 * | 3/2004 | Cense et al. ............ 606/9 | EP | 0755698 | 1/1997 |
| 6,709,269 | B1 | 3/2004 | Altshuler | EP | 0763371 | 3/1997 |
| 6,723,090 | B1 | 4/2004 | Altshuler et al. | EP | 0765673 | 4/1997 |
| 6,743,222 | B2 | 6/2004 | Durkin et al. | EP | 0765674 | 4/1997 |

| | | |
|---|---|---|
| EP | 0783904 | 7/1997 |
| EP | 0885629 | 12/1998 |
| EP | 1038505 | 9/2000 |
| EP | 1219258 | 7/2002 |
| EP | 1226787 | 7/2002 |
| EP | 1 457 234 A2 | 9/2004 |
| GB | 2044908 | 10/1980 |
| GB | 2123287 | 2/1984 |
| GB | 2360946 | 10/2001 |
| JP | 2001145520 | 5/2001 |
| RU | 2082337/95105406 | 6/1997 |
| RU | 2089126/94012665 | 10/1997 |
| RU | 2089127/94040344 | 10/1997 |
| RU | 2096051/95012749 | 11/1997 |
| RU | 2122848/4954402 | 10/1998 |
| WO | WO 86/02783 | 5/1986 |
| WO | WO 90/00420 | 1/1990 |
| WO | WO 92/16338 | 1/1992 |
| WO | WO 92/19165 | 11/1992 |
| WO | WO 93/05920 | 4/1993 |
| WO | WO 95/15725 | 6/1995 |
| WO | WO 95/32441 | 11/1995 |
| WO | WO 96/23447 | 8/1996 |
| WO | WO 96/25979 | 8/1996 |
| WO | WO 97/13458 | 4/1997 |
| WO | WO 98/04317 | 2/1998 |
| WO | WO 98/24507 | 6/1998 |
| WO | WO 98/51235 | 11/1998 |
| WO | WO 98/52481 | 11/1998 |
| WO | WO 99/27997 | 6/1999 |
| WO | WO 99/29243 | 6/1999 |
| WO | WO 99/38569 | 8/1999 |
| WO | WO 99/46005 | 9/1999 |
| WO | WO 99/49937 | 10/1999 |
| WO | WO 00/03257 | 1/2000 |
| WO | WO 00/43070 | 7/2000 |
| WO | WO 00/71045 | 11/2000 |
| WO | WO 00/74781 | 12/2000 |
| WO | WO 00/78242 | 12/2000 |
| WO | WO 01/03257 | 1/2001 |
| WO | WO 01/26573 | 4/2001 |
| WO | WO 01/34048 | 5/2001 |
| WO | WO 01/42671 | 6/2001 |
| WO | WO 01/54606 | 8/2001 |
| WO | WO 02/053050 | 7/2002 |
| WO | WO 02/094116 | 11/2002 |
| WO | WO 04/073537 | 9/2004 |
| WO | WO 04/084752 | 10/2004 |
| WO | WO 04/086947 | 10/2004 |

OTHER PUBLICATIONS

G.B. Altshuler et al., "Extended theory of selective photothermolysis," Lasers in Surgery and Medicine, vol. 29, pp. 416-432, 2001.

R.L. Amy & R. Storb, "Selective mitochondrial damage by a ruby laser microbeam: An electron microscopic study," Science, vol. 15, pp. 756-758, Nov. 1965.

R.R. Anderson et al., "The optics of human skin," Journal of Investigation Dermatology, vol. 77, No. 1, pp. 13-19, 1981.

R.R. Anderson & J.A. Parrish, "Selective photothermolysis: Precise microsurgery by selective absorption of pulsed radiation," Science, vol. 220, pp. 524-527, Apr. 1983.

A.V. Belikov et al., "Identification of enamel and dentine under tooth laser treatment," SPIE vol. 2623, Progress in Biomedical Optics Europe Series, Proceedings of Medical Applications of Lasers III, pp. 109-116, Sep. 1995.

P. Bjerring et al., "Selective Non-Ablative Wrinkle Reduction by Laser," J Cutan Laser Ther, vol. 2, pp. 9-15, 2000.

J.S. Dover et al., "Pigmented guinea pig skin irradiated with Q-switched ruby laser pulses," Arch Dermatol, vol. 125, pp. 43-49, Jan. 1989.

L.H. Finkelstein & L.M. Blatstein, "Epilation of hair-bearing urethral grafts using the neodymium:yag surgical laser," Journal of Urology, vol. 146, pp. 840-842, Sep. 1991.

L. Goldman, Biomedical Aspects of the Laser, Springer-Verlag New York Inc., publishers, Chapts. 1, 2, & 23, 1967.

L. Goldman, "Dermatologic manifestations of laser radiation," Proceedings of the First Annual Conference on Biologic Effects of Laser Radiation, Federation of American Societies for Experimental Biology, Supp. No. 14, pp. S-92-S-93, Jan.-Feb. 1965.

L. Goldman, "Effects of new laser systems on the skin," Arch Dermatol., vol. 108, pp. 385-390, Sep. 1973.

L. Goldman, "Laser surgery for skin cancer,"New York State Journal of Medicine, pp. 1897-1900, Oct. 1977.

L. Goldman, "Surgery by laser for malignant melanoma," J. Dermatol. Surg. Oncol., vol, 5, No. 2, pp. 141-144, Feb. 1979.

L. Goldman, "The skin," Arch Environ Health, vol. 18, pp. 434-436, Mar. 1969.

L. Goldman & D.F. Richfield, "The effect of repeated exposures to laser beams," Acta derm.-vernereol., vol. 44, pp. 264-268, 1964.

L. Goldman & R.J. Rockwell, "Laser action at the cellular level," JAMA, vol. 198, No. 6, pp. 641-644, Nov. 1966.

L. Goldman & R.G. Wilson, "Treatment of basal cell epithelioma by laser radiation," JAMA, vol. 189, No. 10, pp. 773-775.

L. Goldman et al., "The biomedical aspects of lasers," JAMA, vol. 188, No. 3, pp. 302-306, Apr. 1964.

L. Goldman et al., "Effects of laser beam on the skin, Preliminary report" Journal of Investigative Dermatology, vol. 40, pp. 121-122, 1963.

L. Goldman et al., "Effect of laser beam on the skin, III. Exposure of cytological preparations," Journal of Investigative Dermatology, vol. 42, pp. 247-251, 1964.

L. Goldman et al., "Impact of the laser on nevl and melanomas," Archives of Dermatology, vol. 90, pp. 71-75, Jul. 1964.

L. Goldman et al., "Laser treatment of tattoos, A preliminary survey of three year's clinical experience," JAMA, vol. 201, No. 11, pp. 841-844, Sep. 1967.

L. Goldman et al., "Long-term laser exposure of a senile freckle," ArchEnviron Health, vol. 22, pp. 401-403, Mar. 1971.

L. Goldman et al., "Pathology, Pathology of the effect of the laser beam on the skin," Nature, vol. 197, No. 4870, pp. 912-914, Mar. 1963.

L. Goldman et al., "Preliminary investigation of fat embolization from pulsed ruby laser impacts of bone," Nature, vol. 221, pp. 361-363, Jan. 1969.

L. Goldman et al., "Radiation from a Q-switched ruby laser, Effect of repeated impacts of power output of 10 megawatts on a tattoo of man," Journal of Investigative Dermatology, vol. 44, pp. 69-71, 1965.

L. Goldman et al., "Replica microscopy and scanning electron microscopy of laser impacts on the skin," Journal of Investigative Dermatology, vol. 52, No. 1, pp. 18-24, 1969.

M.C. Grossman et al., "Damage to hair follicles by normal-mode ruby laser pulses," Journal of he American Academy of Dermatology, vol. 35, No. 6, pp. 889-894, Dec. 1996.

E. Klein et al., "Biological effects of laser radiation 1.," Northeast Electronics Research and Engineering Meeting, NEREM Record, IEEE catalgue No. F-60, pp. 108-109, 1965.

J.G. Kuhns et al., "Laser injury in skin," Laboratory Investigation, vol. 17, No. 1, pp. 1-13, Jul. 1967.

J.G. Kuhns et al., "Biological effects of laser radiation II Effects of laser irradiation on the skin," NEREM Record, pp. 152-153, 1965.

R.J. Margolis et al., "Visible action spectrum for melanin-specific selective photothermolysis," Lasers in Surgery and Medicine, vol. 9, pp. 389-397, 1989.

J.A. Parrish, "Selective thermal effects with pulsed irradiation from lasers: From organ to organelle," Journal of Investigative Dermatology, vol. 80, No. 6 Supplement, pp. 75s-80s, 1983.

L. Polla et al., "Melanosomes are a primary target of Q-switched ruby laser irradiation in guinea pig skin," Journal of Investigative Dermatology, Vol. 89, No. 3, pp. 281-286, Sep. 1987.

T. Shimbashi & T. Kojima, "Ruby laser treatment of pigmented skin lesions," Aesth. Plast. Surg., vol. 19, pp. 225-229, 1995.

Stratton, K., et al., "Biological Effects of Laser Radiation II: ESR Studies of Melanin Containing Tissues after Laser Irradiation," Northeast Electronics Research and Engineering Meeting—NEREM Record, IEEE Catalogue No. F-60, pp. 150-151, Nov. 1965.

C.R. Taylor et al., "Treatment of tattoos by Q-switched ruby laser," Arch.Dermatol. vol. 126, pp. 893-899, Jul. 1990.

V.V. Tuchin, "Laser light scattering in biomedical diagnostics and therapy," Journal of Laser Applications, vol. 5, No. 2-3, pp. 43-60, 1993.

S. Watanabe et al, "Comparative studies of femtosecond to microsecond laser pulses on selective pigmented cell injury in skin," Photochemistry and Photobiology, vol. 53, No. 6, pp. 757-762, 1991.

A.J. Welch et al., "Evaluation of cooling techniques for the protection of the pidermis during HD-yag laser irradiation of the skin," Neodymium-Yag Laser in Medicine and Surgery, Elsevier Science Publishing Co., publisher, pp. 195-204, 1983.

R.B. Yules et al., "The effect of Q-switched ruby laser radiation on dermal tattoo pigment in man," Arch Surg, vol. 95, pp. 179-180, Aug. 1967.

E. Zeitler and M. L. Wolbarsht, "Laser Characteristics that Might be Useful in Biology," Laser Applications in Medicine and Biology, vol. I, M.L. Wolbarsht, editor, Plenum Press, publishers, Chapter 1, pp. 1-18, 1971.

Abstracts Nos. 17-19, Lasers in Surgery and Medicine, ASLMS, Supplement 13, 2001.

Abstracts Nos. 219-223, ASLMS.

Invention description to certificate of authorship, No. 532304, "The way of investigation of radiation time structure of optical quantum generator".

Invention description to certificate of authorship, No. 719439, "The ring resonator of optical quantum generator".

Invention description to certificate of authorship, No. 741747, "The modulator of optical radiation intensity".

Invention description to certificate of authorship, No. SU 1257475 A1, "Laser interferometric device to determine no-linearity of an index of refraction of optical medium".

Invention description to certificate of authorship, No. SU 1326962 A1, "The way of determination of non-linearity of an index of refraction of optical medium".

Ohshiro et al., "The Ruby and Argon Lasers In The Treatment of the Naevi", Annals Academy of Medicine, vol. 12, No. 2, pp. 388-395 (1983).

* cited by examiner

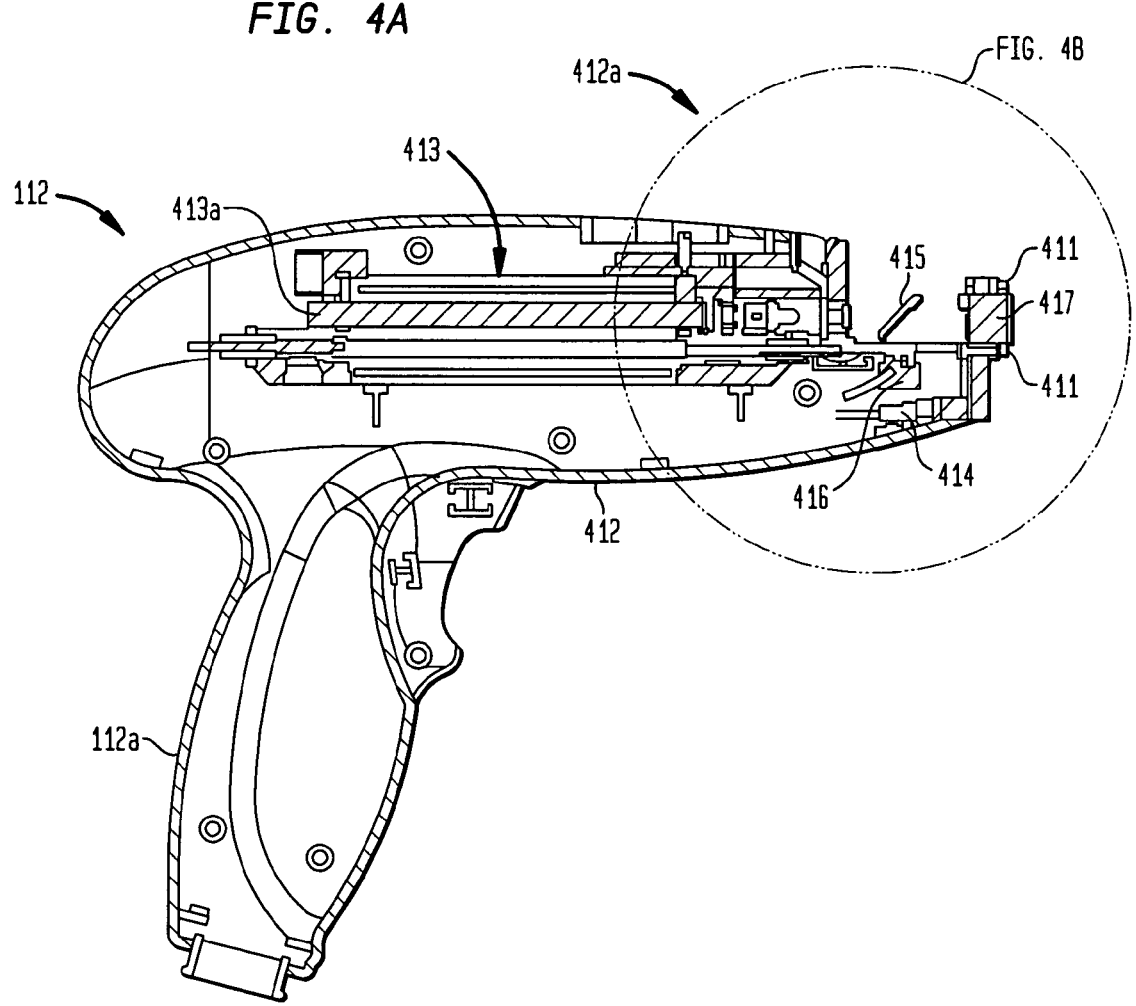

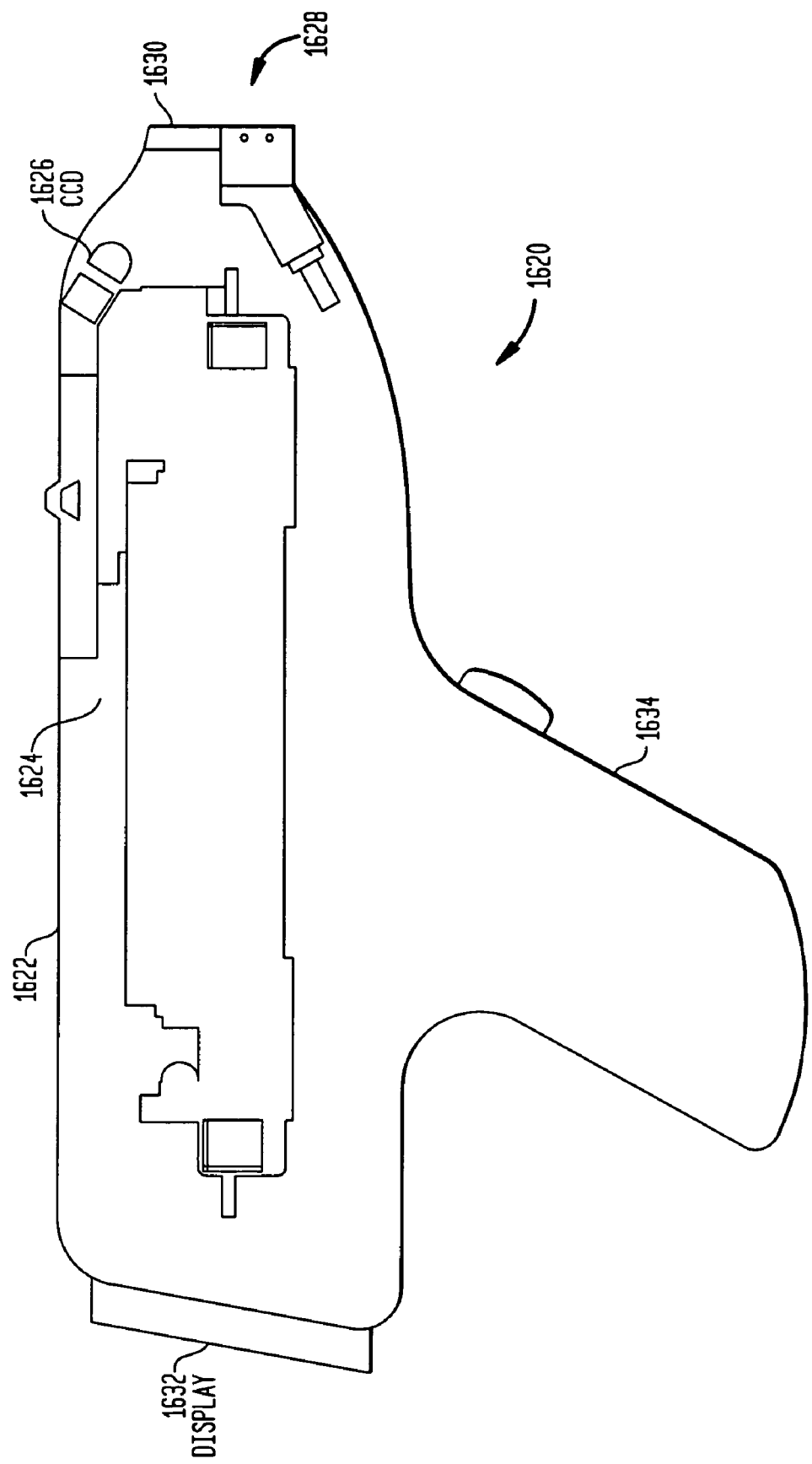

DERMATOLOGICAL TREATMENT WITH VISUALIZATION

RELATED APPLICATION

The present application claims priority to a provisional application entitled "Dermatological Treatment With Visualization" filed on Dec. 31, 2003 and having a Ser. No. 60/534,060.

BACKGROUND OF THE INVENTION

This invention relates generally to methods and apparatus for utilizing energy, e.g., optical radiation, to treat various dermatological and cosmetic conditions. More particularly, the invention provides a handheld dermatological device that facilitates viewing and measuring parameters of a treatment area before, during, and after application of a treatment modality.

Energy such as electromagnetic, mechanical, thermal, acoustic, and particle beam radiation has been utilized for many years in medical and non-medical facilities to treat various medical and cosmetic conditions. Such treatments include, but are not limited to, hair growth management, including limiting or eliminating hair growth in undesired areas and stimulating hair growth in desired areas, treatments for PFB (razor bumps), skin rejuvenation, anti-aging treatments including improving skin texture, elasticity, wrinkles and skin lifting and tightening, pore size reduction, reduction of non-uniform skin pigmentation, improving vascular and lymphatic systems, treatment of vascular lesions such as spider veins, leg vein, varicose veins, port wine stain, rosacea, telangiectasia, removal of pigmented lesions, repigmentation, improved skin moistening, treatment of acne including non-inflammatory, inflammatory and cysts, treatment of psoriasis, reduction of body odor, reduction of oiliness, reduction of sweat, reduction/removal of scars, prophylactic and prevention of skin diseases, including skin cancer, improvement of subcutaneous regions, including fat reduction and cellulite reduction, as well as numerous treatments for other conditions.

The treatments can be performed, for example, by employing optical energy (including ultraviolet, visible, and infrared), microwave energy, radiofrequency, low frequency or DC current energy, acoustic energy, mechanical energy and kinetic energy of particles (for example, sapphire particles), skin cooling or heating. The flow of energy can be delivered to the treatment region via a handpiece, which can include a housing, energy distribution system (comprising, for example, a radiation source, optics and a scanner), and an optional skin cooling element. In rare cases, the handpiece can also include a diagnostic sensor (i.e., skin temperature radiometer). The diagnostic sensor in such systems is used to protect the skin from unwanted damage (i.e., due to overheating or over cooling).

While various handheld devices have been disclosed for applying dermatological treatments, currently, present systems lack efficient mechanisms for positioning the treatment head of the handpiece over a selected target treatment area and/or viewing the target area while a treatment modality is being applied. Further, such conventional handheld devices lack systems for preferential imaging of subsurface skin tissue.

Accordingly, there exists a need for handheld dermatological devices that provide mechanisms for positioning the device's treatment head over a target area and/or viewing the target area even as the treatment is being applied.

There is also a need for such handheld dermatological devices that can provide better targeting and evaluation of a treatment target and surrounding tissue before, during, and after treatment to improve efficacy and safety of the treatment and provide an opportunity for self treatment with a cosmetic device suitable for home use.

SUMMARY OF THE INVENTION

Methods and devices for treating dermatological or cosmetic conditions that include imaging a target skin region, e.g., skin tissue, are disclosed that allow preferential illumination of the skin region, obtaining its image and displaying it to a user for better alignment of flow of a treatment energy relative to a target region and performing diagnostic of the target before, during and after treatment. A user of such devices can be, for example, a physician, an aesthetician, or a person who can utilize the device for self treatment of a cosmetic condition. In some embodiments, the device provide diagnostic functionality. In some embodiments, the devices include handheld devices that can, in addition to imaging capability, provide treatment energy to a subject's skin. The term "treatment energy" as used herein can refer to therapeutic energy to treat diseased condition or energy suitable for treating cosmetic conditions.

In one aspect, a handheld dermatological device is disclosed that allows application of treatment energy to a target skin region as well as visualizing the skin treatment region prior to, during, or after application of the treatment energy. Such a device can include, for example, an image capture device and a display device that is mounted to a housing of the handheld device and is coupled (electrically, optically or otherwise (wireless)) to the image capture device to present acquired images to a user, e.g., a medical professional or a consumer. The image capture device can be connected to the display through a microprocessor, which can be integrated with the display or the image capture device itself. The handheld device can further include a head that can be precisely aligned by a user relative to a patient's skin by utilizing one or more images presented in the display, and through which treatment energy can be applied to a target skin region.

A dermatological device, as used herein, can refer to a therapeutic device or a cosmetic device, including a home cosmetic device.

In one aspect, a handheld dermatological device is disclosed that includes a housing capable of being manually manipulated to position a head portion thereof in proximity to a person's skin, and is adapted for delivery of treatment energy to a target skin region. The handheld device can further include an illumination source coupled to the housing for generating radiation to illuminate the target skin region, and a detector disposed in the housing and adapted to primarily detect tissue scattered radiation emanating from the target skin region. As used herein, the term "primarily detect tissue scattered radiation emanating from the target skin region" is intended to mean detecting radiation from the illumination source that is primarily scattered by tissue below and around the target skin region depth and thus reaches the detector from beneath the skin surface thereby emanating or coming from the target skin region. This may also be referred to as "translucent radiation" where the radiation is coming from below the target skin region to make the target skin region more visible. The term "primarily" in this context is used to distinguish between such tissue scattered radiation and light that reaches the detector by reflection of illuminating or ambient light from the surface of the skin and skin above the target skin region.

Thus, "primarily" typically means greater than 50%, preferably greater than 60%, more preferably greater than 70%, more preferably greater than 80%, more preferably greater than 90%, more preferably greater than 95%, of the detected radiation corresponds to scattered radiation emanating from below and around the target skin region depth as opposed to light reflected by the skin surface and scattered from the skin above depth of target skin region.

The detector can be positioned relative to the illumination source so as to primarily detect the scattered radiation. The detector can optionally include an image capture device for generating an image of the target skin region. Further, a display can be mounted to the housing for displaying the image.

The illumination source can be adapted to deliver radiation to a first skin surface segment so as to illuminate the target region such that at least a portion of the scattered radiation reaches the detector via a second skin surface segment. A shield mounted to the head portion can shield the second skin surface segment from direct (via skin surface) application of radiation from the illumination source. In some embodiments, the device can further include additional illumination sources. In some cases, the illumination sources can be selected to generate radiation with different wavelengths. A control unit can be further included for selectively activating at least one, or more of the illumination sources. For example, the control unit can activate the illumination sources according to a preset temporal pattern.

In some embodiments, the housing can include an aperture through which the scattered radiation can reach the detector. The illumination source is preferably offset relative to the aperture such that illuminating radiation reaches the target region along different paths than those along which scattered light from the target region is collected by the detector. In some embodiment, the illumination source can be positioned at an angle relative to an optical axis of the device In other aspects, a treatment source can be disposed in the housing for generating the treatment energy. By way of example, the treatment source can generate electromagnetic radiation having one or more wavelengths in a range of about 290 nm to about 3000 nm, or preferably in a range of about 500 to about 3000 run, or preferably in a range of about 600 nm to about 1900 nm, or more preferably in a range of about 800 nm to about 1100. The treatment source can generate pulsed radiation having a fluence in a range of about 1 to about 200 $J/cm^2$ with pulse widths in a range of about 1 ns to about 10 seconds. For example, the treatment source can be a neodymium (Nd) laser, such as a Nd:YAG laser.

In another aspect, the housing can be adapted for receiving the treatment energy from an external treatment source, such as a radiation source. For example, the device can further include an optical fiber for directing radiation from an external treatment source to the target skin region. Optical fiber can be utilized for delivery of illumination light from illuminating sources to the skin.

In further aspects, the device can further include a first polarizer coupled to the illumination source and a second polarizer coupled to the detector, wherein the polarizers have substantially orthogonal or parallel polarization axes.

In another aspect, the device can further include a radiation guiding that is adapted to contact a skin surface region. The illumination source can be optically coupled to the guiding element for coupling radiation into the guiding element so as to generate illumination waves refractively coupled to at least a portion of the target region. A polarizer can be coupled to the detector to substantially prevent radiation reflected from the skin surface region from reaching the detector while allowing detection of radiation scattered from the target region in response to the refractively coupled waves. The device can further include another polarizer coupled to the illumination source having a polarization axis substantially orthogonal to that of the polarizer coupled to the detector.

In another aspect, a method of treating a target skin region is disclosed comprising illuminating the target skin region, detecting primarily tissue scattered radiation emanating from the target region in response to the illumination, and directing treatment energy to at least a portion of the target skin region. A first portion (segment) of skin surface can be illuminated with illuminating radiation propagating along a first direction such that at least a portion of the radiation penetrates the skin tissue below a second segment of skin surface. The second segment of the skin surface can be shielded from direct application of the radiation. The scattered radiation can be detected along a second direction offset relative to the first direction. The radiation emanating from the second segment of skin surface can be detected to obtain an image of the target skin region. The image can be used to align a treatment energy beam with a portion of skin tissue in the target skin region so as to apply treatment energy to that portion. By way of example, the illumination radiation can be selected to have one or more wavelengths in a range of about 290 nm to about 3000 nm. One or more images of the target skin region can be monitored before, during or after application of the treatment energy.

In another aspect, a handheld dermatological device is disclosed comprising a housing capable of being manually manipulated to position a head portion thereof in proximity to a person's skin surface, an illuminating source mounted to the housing for illuminating a target skin region, a neodymium (Nd) laser, e.g., a Nd:YAG laser, disposed in the housing for generating radiation, an optical system coupled to the laser for directing radiation from the laser to the target skin region, an image capture device mounted in the housing for generating an image of the illuminated target skin region, and a display coupled to the housing and in communication with the image capture device to display the image. The device can further include a shield mounted to the head portion for shielding a portion of a skin surface through which the image capture device obtains an image of the target skin region from direct illumination by the illumination source. A zoom lens system coupled to the laser can adjust a dimension, e.g., a diameter, of a radiation beam generated by the laser. The device can further include a microprocessor in communication with the image capture device for processing one or more images obtained by the image capture device. The image capture device can be a CCD camera, a video camera or any other suitable analog or digital imaging system. The device can also include imaging optics optically coupled to the image capture device for directing at least a portion of radiation emanating from the target skin region to the image capture device. In some embodiments, the device further includes additional illumination sources. In some cases, the illumination sources can generate radiation with different wavelengths. A control unit can be further included for selectively activating the illumination sources according to a desired temporal pattern so as to illuminate the target region with radiation having different wavelengths and/or from different angles.

In another aspect, a method of treating skin is disclosed comprising applying treatment radiation, for example, radiation generated by a neodymium (Nd) laser (e.g., Nd:YAG) to selected vasculature located in a target skin region, generating an image of the target skin region, and displaying the image. In another aspect, a method of treating skin is disclosed that comprises applying fluorescence or pumping radiation from sources providing treatment energy, for example, fluorescence from a neodymium (Nd) laser, to illuminate a target skin region, generating an image of the target region, and displaying the image. As used herein, the term "treating skin" is intended to encompass both medical and cosmetic treatments, such as hair removal, hair growth management, removal of vascular lesions (e.g., telangiectasia, psoriasis, rosacea, spider vein, leg vein), pigmented lesions, treatment of nail disorders, fat reduction, acne treatment, skin rejuvenation, wrinkle reduction and tattoo removal and the like. The image can be displayed before, during or after application of the treatment radiation. The image can be used to align a treatment radiation beam with the selected vasculature.

In another aspect, a handheld dermatological device is disclosed comprising a housing, a source disposed in the housing for generating both treatment radiation and illuminating radiation, an optical system for directing the treatment and illuminating radiation to a target skin region, an image capture device mounted in the housing for acquiring an image of the target region, and a display mounted to the housing for displaying the image. By way of example, the source can include a Nd:YAG laser. The Nd:YAG laser can generate lasing treatment radiation and the laser rod can generate fluorescence illumination radiation. The image capture device can be adapted to detect scattered radiation emanating from the target skin region in response to illumination by the illuminating radiation.

In another aspect, a handheld dermatological device is disclosed comprising a housing through which treatment energy can be applied to a skin target region, an illumination source coupled to the housing for illuminating the target region, an image capture device mounted in the housing for acquiring one or more images of the target region, goggles suitable for wearing by an operator of the device. The goggles can incorporate one or more display devices in communication with the image capture device for displaying the images to the operator. The device can include a treatment source disposed in the housing. Alternatively, the housing can be adapted to receive the treatment energy from an external source, e.g., via an optical fiber or other energy delivery systems.

In another aspect, a handheld dermatological device is disclosed comprising a housing through which treatment energy can be applied to a target skin region, an illumination source coupled to the housing for generating radiation for delivery to a first skin surface segment to illuminate the skin target region such that at least a portion of radiation emanating from the target region in response to the illumination reaches a second skin surface segment, and an image capture device capable of detecting the portion of radiation emanating from the target region to form an image thereof. The device further can further comprise a treatment source disposed in the housing for generating the treatment energy. The treatment source can be a laser or a broadband source, such as LED or lamps. In some embodiments, the device further comprises a shield for shielding the second skin surface segment from direct application of the illumination radiation. For example, the shield can be disposed in proximity of the illumination source to substantially prevent direct illumination of the second skin surface segment.

In another aspect, the invention discloses a method for treating a target region of skin tissue comprising illuminating a first skin surface with radiation such that at least a portion of the radiation penetrates the skin tissue below a second skin surface, shielding the second skin surface from direct application of the radiation, detecting radiation emanating from the second skin surface to obtain an image of the target skin region, and directing treatment energy to the target skin region through the second skin surface.

In yet another aspect, the invention discloses a handheld dermatological device comprising a housing for applying treatment energy to a portion of a person's skin surface to treat a target skin region, an illumination source coupled to the housing for illuminating the target skin region from below the portion of the skin surface, and a shield disposed in the housing so as to substantially prevent the illumination source from directly illuminating the portion of the skin surface from above the portion of the skin surface. The device can further include a detector mounted in the housing to detect at least a portion of the illumination radiation scattered by the target skin region. For example, the detector can be positioned in the housing so as to detect at least a portion of the illumination radiation emanating from the portion of the skin surface.

In another aspect, a dermatological device is disclosed comprising a housing through which treatment energy can be applied to a target skin region, a radiation guiding element coupled to the housing and adapted to contact a skin surface region, at least one illumination source optically coupled to the guiding element for coupling radiation into the guiding element so as to generate illumination electromagnetic radiation (wave) refractively coupled to at least a portion of skin in contact with the guiding element, and an image capture device capable of detecting radiation scattered from the target region in response to the refractively coupled illumination radiation. The image capture device can form an image of the target region. The radiating guiding element can be formed of any suitable transparent material as discussed in more detail below. For example, the guiding element can be formed of sapphire or quartz and can have an index of refraction in a range of about 1.3 to about 1.9. In another aspect, images exhibiting interruptions of total internal reflection of illumination light at the contact surface of the guiding element and skin surface can be used for visualization of targets on the skin surface. The device can further comprise a polarizer coupled to the image capture device so as to prevent radiation having a selected polarization from reaching the image capture device. A filter coupled to the image capture device can be included in the device so as to prevent radiation having one or more selected wavelengths from reaching the image capture device.

In another aspect, a method of treating person's skin is disclosed comprising placing an optical guidance element on a portion of the skin surface, coupling illuminating radiation into the guidance element so as to generate refractively coupled waves penetrating a subsurface region below the portion of the skin surface, detecting at least a portion of radiation scattered by the subsurface region in response to the refractively coupled waves to form an image of the subsurface region, and directing treatment energy to at least a portion of the subsurface region.

In a related aspect, radiation can be coupled to the guidance element so as to generate evanescent waves at the interface of the guidance element with the skin. Such waves can be utilized for imaging and diagnosis of dermatological structures and conditions, as discussed in more detail below.

In another aspect, a handheld dermatological device is disclosed comprising a housing through which treatment energy can be applied to a person's skin, two illumination sources capable of generating radiation having at least two different wavelengths, the sources being mounted to a head portion of the housing for illuminating a target skin region, a control unit for selectively activating the sources, and an image capture device disposed in the housing for detecting at least a portion of radiation scattered by the target skin region in response to illumination by at least one of the sources. The control can be adapted for activating the sources in different temporal intervals and/or for triggering the image capture device to form an image of the target region upon activation of at least one of the sources. The device can include a shield positioned in proximity of at least one of the illumination sources for shielding a selected skin surface segment from direct illumination by that source. The image capture device can be adapted to collect radiation via the shielded skin surface segment radiation scattered by the target skin region. The device can further include a treatment source disposed in the housing for applying treatment energy to the target skin region through the shielded skin surface segment.

In another aspect, the invention provides a device for imaging a subsurface target region of skin tissue that includes an illumination source for illuminating a skin surface with illuminating radiation such that at least a portion of the radiation penetrates the skin tissue below the surface and is at least partially scattered by the skin tissue. The device can further include a detector that is capable of detecting radiation scattered by the subsurface target region, and a shield for shielding the detector from illuminating radiation that is directly reflected by the skin surface. The detector can comprise an image capture device that can generate an image of the subsurface target region. Any suitable image capture device can be employed. For example, the image capture device can be a CCD/CMOS camera or a video camera.

The device can include a handheld housing through which treatment energy can be directed to the skin. The treatment energy can be provided by a source mounted to the housing, or alternatively, it can be provided by an external source and guided through a path within the housing to the skin. In some embodiments, the treatment source is a radiation source, such as a laser or a broad band source (e.g., a lamp, LED).

In a related aspect, in the above imaging or the handheld device, the shield can comprise a polarizer coupled to the detector to prevent radiation having a selected polarization direction from reaching the detector. In some embodiments, another polarizer having a polarization axis orthogonal or parallel to the shield polarizer, can be coupled to the illumination source. Alternatively, the shield can be formed from a material that is substantially opaque to the radiation generated by the illumination source, and can be placed in proximity of the illumination source to prevent direct illumination of a portion of the skin surface of the target region.

In further aspects, the invention provides a method for imaging a subsurface target region of skin tissue that includes illuminating a skin surface with illumination radiation such that a significant portion of the radiation penetrates the skin tissue below the surface and is at least partially scattered by that tissue while minimizing scattering signal from skin tissue located deeper than the target tissue. A detector is positioned so as to detect at least a portion of radiation scattered by the subsurface target region. The detector is shielded from illumination radiation that is directly reflected by the skin surface (and scattered from tissue above the target region depth) while enhancing detection of radiation that is primarily scattered by tissue below and around target skin region depth, and an image of the subsurface target region is obtained based on the detected scattered radiation. The illumination radiation can have one or more wavelengths in a range of about 350 nm to about 2000 nm. The illumination sources can be, for example, light emitting diodes (LED), diode lasers, lamps, or other suitable sources of electromagnetic energy. In some cases, treatment energy, e.g., radiation having one or more wavelengths in a range of about 290 nm to about 20,000,000 nm, can be applied to the subsurface target region in conjunction with monitoring one or more images of this region prior to, during, and/or after application of the treatment energy.

In a related aspect, the invention provides a handheld dermatological device that includes a housing capable of being manually manipulated to direct treatment energy to a skin target region, an image capture device coupled to the housing to generate an image of at least a portion of the target region, and a display device mounted to the housing and electrically coupled to the image capture device to display images captured by the image capture device. The term "mounted," as used herein, is intended to encompass mechanical coupling to the housing such that the housing and the display can be simultaneously, or separately, manually manipulated by the user to direct treatment radiation to a target area and/or view the target. The housing can further comprise a head capable of transmitting the treatment energy. The user can precisely position the head over a desired portion of the treatment region by using the display as a guide. The user can therefore diagnose and/or view the treatment region before, during and after treatment more effectively. Thus, more effective and safer treatment will be possible than are currently available as the user can directly monitor the results of the treatment in real-time.

In some embodiments, the handheld device can include an optical system, such as an objective, optical filter, spectral filter, spatial filter, polarizer, phase elements, masks and illumination system for facilitating acquisition of images and/or enhancing their presentation. For example, such an optical system can be disposed between the image capture device and the patient's skin to prevent radiation having selected wavelengths and/or polarizations from reaching the image capture device.

Further, an image of the treatment region can be processed by an image processor and/or a microprocessor, for example, to enhance its resolution (or contrast), color and brightness. For example, the microprocessor can be positioned between an image capture device and a display. In some embodiments, the microprocessor can be coupled to the image capture device such that the user can be alerted when a treatment has reached a desired preset limit. The microprocessor can provide image processing for magnification, improved contrast of the image, and/or synchronization of the image capture with skin illumination, as discussed in more detail below. For example, the image capture device can send multiple images of the treatment region during treatment to the microprocessor. The microprocessor can compare changes in selected parameters of the treatment region to threshold values previously stored, for example, in a database. Various parameters, such as color or a change of fluorescence emission, can be used to monitor the applied treatment. Skin conditions, such as, pigmented lesions, spider veins, port wine stains, psoriasis, can change color during and after treatment. The treatment radiation can also coagulate and/or destroy vessels resulting in a color change in images of such vessels. Additionally, treatment of acne can be monitored through a measurement of fluorescence.

Among microbial population of pilosebaceous unit, most prominent is *Propionibacterium Acnes* (*P. Acnes*). These bacteria are causative in forming inflammatory acne. *P. Acnes* can exhibit fluorescence. Upon treatment, the fluorescence will decrease.

Images of the treatment region can be stored in a memory card, which can be attached to the microprocessor, or sent to a computer via a wireless or hard-wired connection. These images can be used to compile a patient or treatment history file.

In some embodiments, the display device can be fixedly mounted onto the housing. In other embodiments, the display device can be hingedly attached to the housing. For example, the display device can be attached to a railing or flexible wire such that the display device can be extended by the user for ease of viewing and can be folded for ease of storage. Such an adjustable display device can be utilized, for example, by a patient for self-treatment In other aspects, the displays can be built into goggles to be worn by a user or a patient. The display device can be permanently attached to the housing of the handheld device, or it can be mounted to the housing in a removable and replaceable manner. In some embodiments, a large display can be used for providing better image resolution, and facilitating simultaneous observation of an image by an operator and a patient.

The image capture device can detect a change in at least one of optical signals, infrared, electro capacitance, or acoustic signals. An electro capacitor image capture device can be preferable for skin surface and epidermis imaging. The image capture device can be either an analog or digital device. In some embodiments, the image capture device is a camera. In a preferred embodiment, the image capture device is a CCD/CMOS camera or a video camera.

A handheld dermatological device according to the teachings of the invention can be utilized to deliver different types of treatment energy to a patient. Some exemplary optical radiation wavelengths and examples of conditions that can be treated by these wavelengths are provided in Table 1 below.

TABLE 1

Preferred parameters for the treatment of dermatological conditions with light.

| Treatment condition or application | Wavelength, nm |
|---|---|
| Anti-aging | 400–11000 |
| Superficial vascular | 290–600 |
|  | 1300–2700 |
| Deep vascular | 500–1300 |
| Pigmented lesion, de pigmentation | 290–1300 |
| Skin texture, stretch mark, scar, porous | 290–2700 |
| Deep wrinkle, elasticity | 500–1350 |
| Skin lifting | 600–1350 |
| Acne | 290–700, 900–1850 |
| Psoriasis | 290–600 |
| Hair growth control, | 400–1350 |
| PFB | 300–400, 450–1200 |
| Cellulite | 600–1350 |
| Skin cleaning | 290–700 |
| Odor | 290–1350 |
| Oiliness | 290–700, 900–1850 |
| Lotion delivery into the skin | 1200–20000 |
| Color lotion delivery into the skin | Spectrum of absorption of color center and 1200–20000 |
| Lotion with PDT effect on skin condition including anti cancer effect | Spectrum of absorption of photo sensitizer |
| ALA lotion with PDT effect on skin condition including anti cancer effect | 290–700 |

TABLE 1-continued

Preferred parameters for the treatment of dermatological conditions with light.

| Treatment condition or application | Wavelength, nm |
|---|---|
| Pain relief | 500–1350 |
| Muscular, joint treatment | 600–1350 |
| Blood, lymph, immune system | 290–1350 |
| Direct singlet oxygen generation | 1260–1280 |

In embodiments in which the treatment energy is applied as pulses, the pulsewidths can be in a range of about 1 nanosecond to about 10 seconds and the pulses can have a fluence in a range of about 1 to about 200 $J/cm^2$.

In other aspects, the invention provides a dermatological imaging device that includes a radiation guiding element that is adapted to contact a skin surface region to provide refractive coupling of light into the skin (refractive illumination). The device can further include at least one illumination source that is optically coupled to the guiding element for coupling radiation into the guiding element so as to generate electromagnetic waves penetrating into a controlled depth of subsurface skin region. The device also includes an image capture device that is capable of detecting radiation scattered from the subsurface skin region in response to the refractive wave illumination. The image capture device can form an image of the subsurface skin region by employing the detected radiation. Further, in some embodiments, a filter and/or a polarizer can be coupled to the image capture device to prevent radiation having a selected polarization, or one or more selected wavelengths, from reaching the image capture device. The refractive coupling of radiation into the skin can be utilized for precise control of treatment and/or imaging of skin surface conditions and/or features, such as, stratum corneum structure, pores, sebaceous follicle openings, hair follicle openings, skin texture, wrinkles, psoriasis. By controlling the refractive index of the guiding element and the incident angle of radiation coupled into the guiding element at the contact surface of the guiding element and the skin, the imaging contrast of a visualized target can be enhanced, as discussed in more detail below.

In further aspects, the invention provides a handheld dermatological device that includes a housing through which treatment energy can be applied to a patient's skin, and further includes one or more sensors mounted to a head portion of the housing, which are capable of generating a dielectric image of a target skin region. Such a dielectric image can provide a distribution of dielectric sensitivity of the skin surface of a target skin region, which can be measured, e.g., by an electro capacitor image capture device. The device can further include a display for displaying the dielectric image. In some embodiments, one or more transducer elements can be coupled to the housing for applying an electric current or acoustic energy to the patient's skin.

In another aspect, the invention provides a handheld dermatological device having a housing through which treatment energy can be applied to a patient's skin, and two or more illumination sources that generate radiation having wavelengths in different wavelength bands. The sources are mounted to a head portion of the housing for illuminating a target skin region. The handheld device can further include a control for selectively activating the sources and a image capture device disposed in the housing for detecting at least a portion of radiation scattered by the target skin region in response to illumination by one or both of the sources.

Further understanding of the invention can be obtained by reference to the following detailed description in conjunction with the associated drawings, described briefly below.

DETAILED DESCRIPTION

The present invention relates generally to dermatological devices, and more particularly to handheld dermatological devices for applying a variety of treatment modalities to a patient's skin while allowing a user to view the treatment area and target before, during, and after application of the treatment. In some embodiments, the handheld device can include one or more radiation sources for illuminating a target region of the patient's skin so as to facilitate imaging that region by an image capture device, and can further include a display in which an image of the target region can be presented.

Figure 1A:
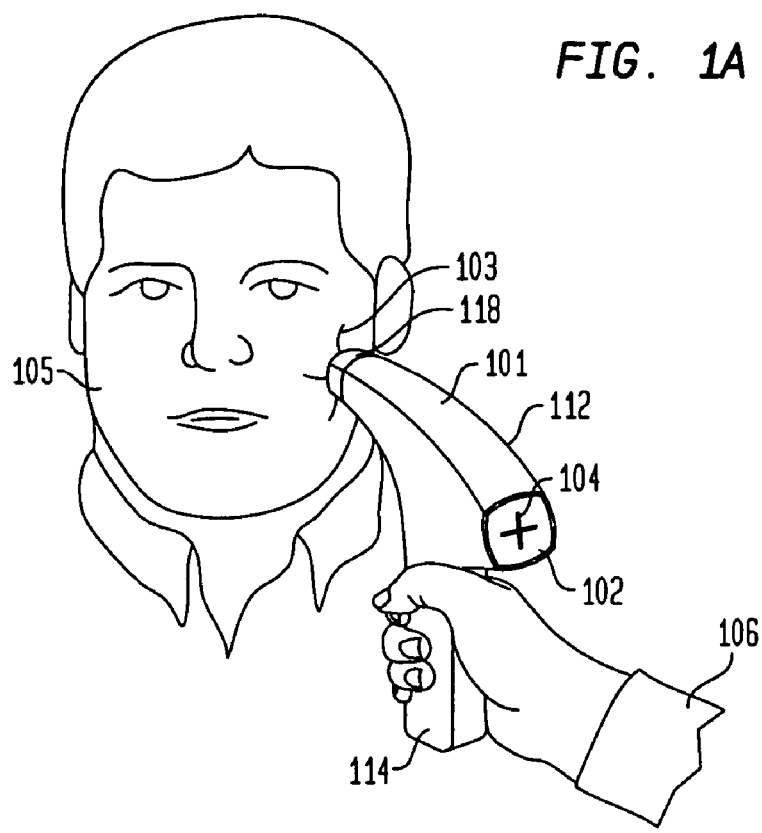
FIG. 1A schematically depicts a handheld device according to one embodiment of the invention, FIG. 1B schematically depicts a handheld device according to one embodiment of the invention having a display movably mounted to the device's housing, FIG. 1C schematically illustrates a handheld device according to one embodiment having a display electrically or optically coupled to the device's housing via one or more flexible wires or optical cables, FIG. 1D schematically illustrates a handheld device according to one embodiment of the invention having a display hingedly attached to the device's housing, FIG. 1E schematically depicts a handheld device according to one embodiment of the invention having a display incorporated in goggles suitable for wearing by a user, FIG. 2A schematically depicts a handheld device according to one embodiment of the invention having a housing through which therapeutic energy can be applied to the skin and an image capture device for generating an image of a target skin region, FIG. 2B schematically depicts a handheld device according to another embodiment of the invention having an illumination source for illuminating a target skin region and an image capture device for acquiring an image of the target region, FIG. 2C schematically illustrates a device according to another embodiment having an illumination source and image capture device for preferentially illuminating and obtaining an image of a target skin region, FIG. 2D schematically illustrates a device according to an embodiment of the invention having a cooling or heating element for applying heat to or extracting heat from the skin and an image capture device for generating an image of a target skin region, FIG. 2E schematically illustrates a device according to another embodiment of the invention having a plurality of radiation sources adapted for preferentially illuminating a subsurface skin region and an image capture device for generating an image of that region, FIG. 3A schematically illustrates a device according to one embodiment of the invention in which polarized radiation is employed for preferential illumination of a target skin region, FIG. 3B schematically illustrates a device according to one embodiment of the invention having a plurality of illumination sources for illuminating a subsurface skin region and a shield disposed in proximity of the sources for shielding a selected skin surface from direct illumination by the sources.

FIG. 1A schematically depicts a handpiece device 112 according to one embodiment of the invention having a housing 101 that includes a handle 114 that allows a user 106, e.g., a medical professional or a home user, to hold and aim the device at a selected target treatment area 103. The housing, which defines an enclosure in which various components of the device are incorporated, is described in more detail below. The housing 101 can include a head or tip portion 118 at a proximal end that can be placed in proximity to, or in contact with, the treatment area 103 (which can be a surface or subsurface region) of a patient 105 to apply a selected treatment energy (e.g., electromagnetic energy, acoustic, particles, etc.) thereto. A display 102 for displaying an image of the treatment area, e.g., at a selected magnification, is coupled to the distal end of the housing 101. The display 102 can be employed to view the treatment area 103, which, in this embodiment, includes two crossing veins, before, during, and after the treatment, as seen in magnified image 104. The treatment area can be located at a depth below the patient's skin surface (including a shallow subsurface region), or can be on the skin surface itself.

Figure 1B:
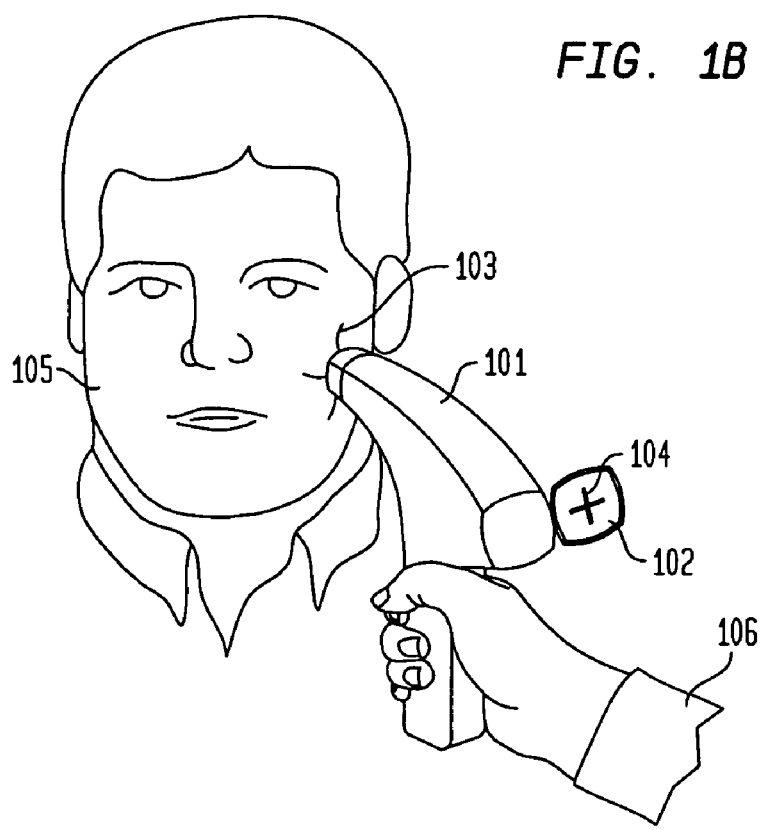
Figure 1C:
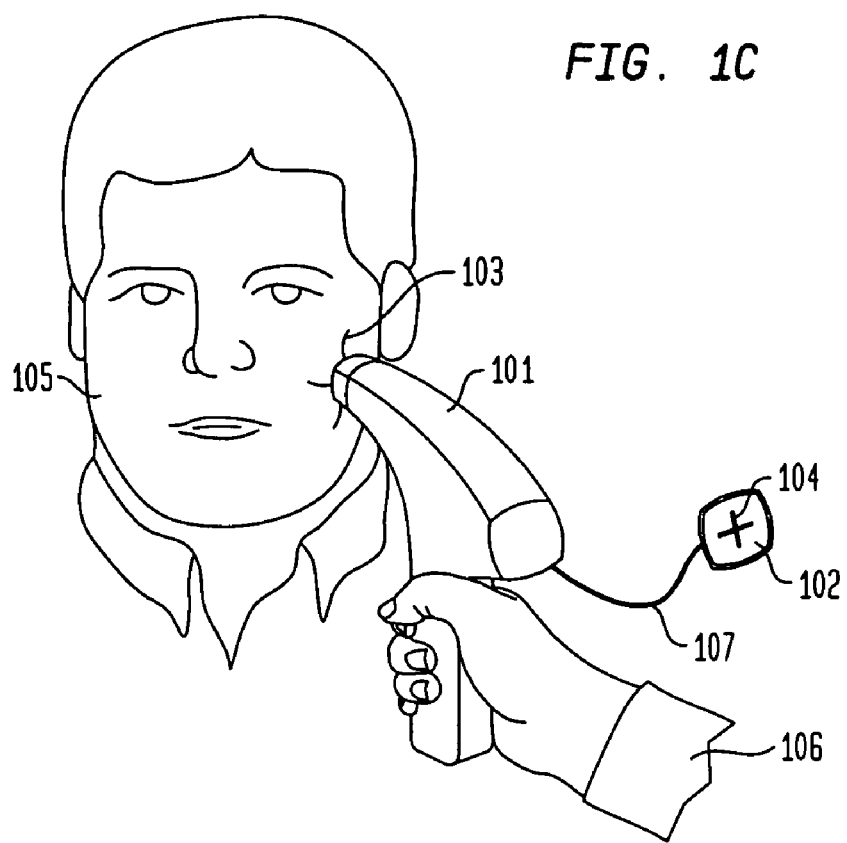
Figure 1D:
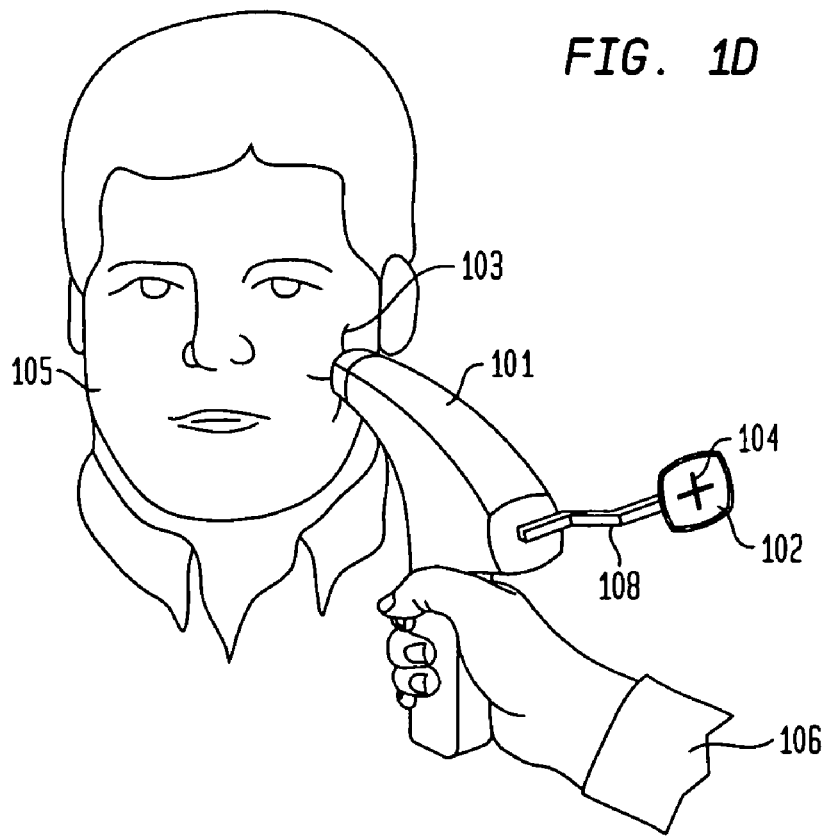
Figure 1E:
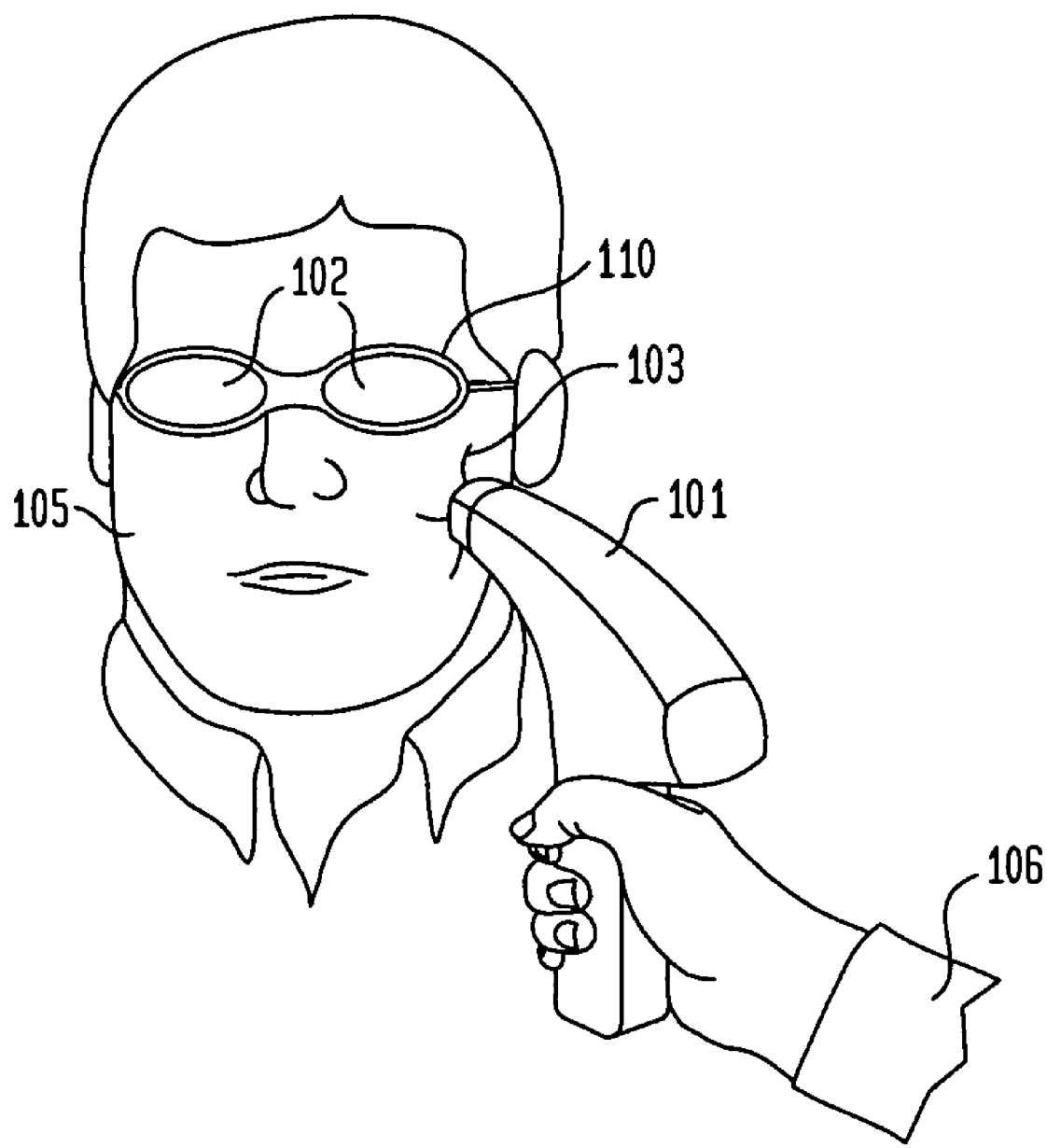

Although the display 102 is fixedly attached to the housing in this embodiment, in another embodiment shown schematically in FIG. 1B, the display 102 is moveably mounted to the housing 101 to allow adjustment of its position relative to a viewer 106, e.g., a person applying the treatment, for flexible viewing of the treatment area. In another embodiment shown in FIG. 1C, the display 102 is mechanically and electrically or optically coupled to the housing 112 via one or more flexible wires or optical cable 107, or alternatively, electrically coupled to the housing 112 via wireless, e.g., WiFi connections. In another embodiment shown in FIG. 1D, the display 102 is hingedly attached to the housing 101 via one or more rails 108 or flexible or bendable material for ease of positioning and storage. In some embodiments, the display 102 is removable from the housing 101. Alternatively, as shown in FIG. 1E, the display 102 can be incorporated in glasses 110 that can be worn by the operator (e.g., medical or other professionals or the patient or customer themselves) to view the treatment area. The glasses can be attached to the housing 101 via a wire, or an optical cable (not shown) or can receive the images via a wireless connection. In some embodiments, the operator 105 can use the device to treat himself as shown on FIG. 1E. In some embodiments, two displays are be mounted in the glasses, each corresponding to one eye of the operator. The two displays can be adapted for stereoscopic viewing of the images (three-dimensional vision).

Figure 2A:
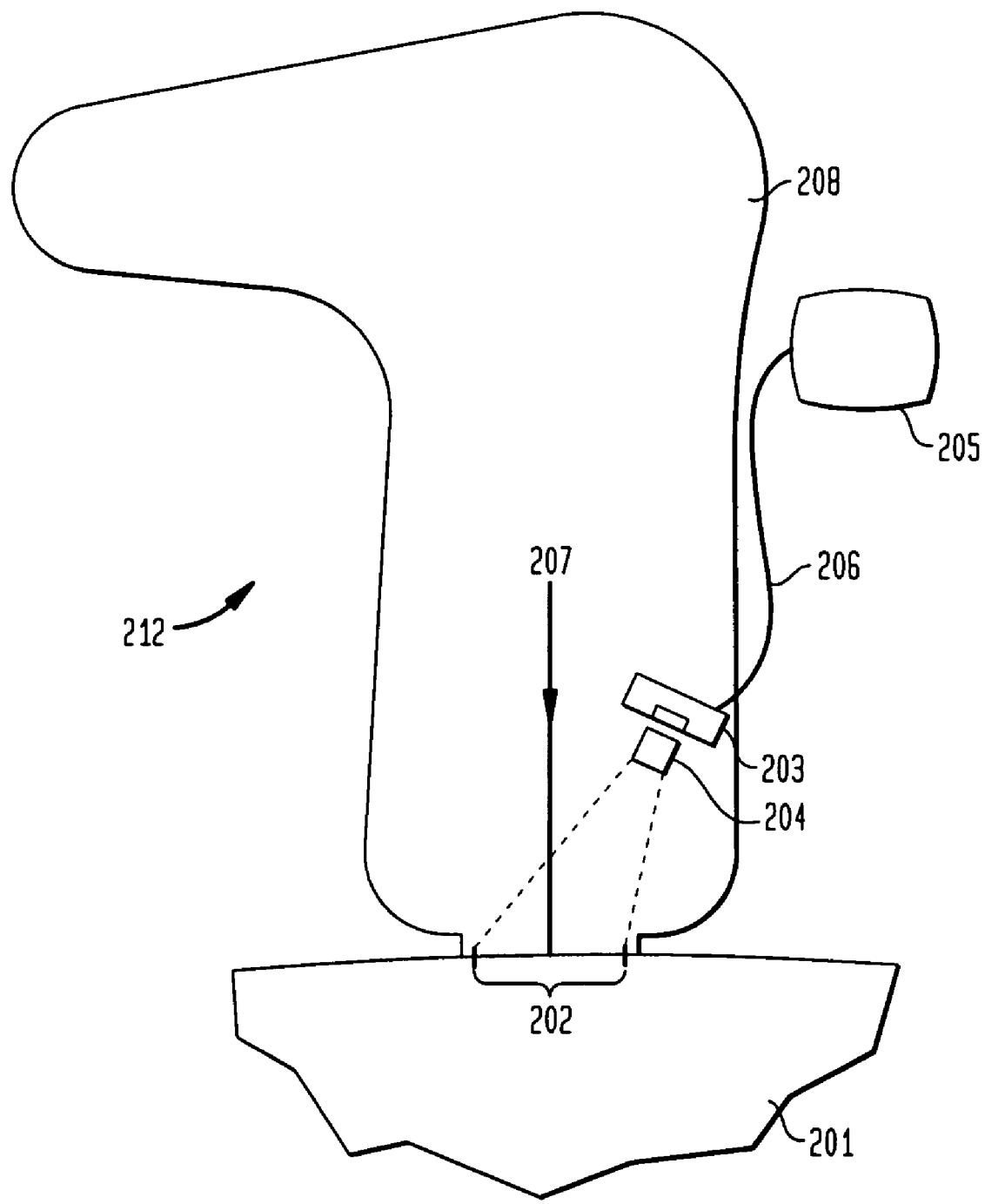

FIG. 2A schematically illustrates that a selected energy flow 207, for example, acoustic, electromagnetic, or kinetic energy, can be directed by a handpiece device 212 according to one embodiment of the invention to a target treatment area 202. A source for generating the applied energy (not shown) can be incorporated in a housing 208 of the device, or alternatively, it can be remotely located relative to the handpiece with its generated energy transmitted via a suitable element, e.g., a waveguide, to the handpiece's housing for delivery to the treatment area. An optical system 204, which can include, e.g., one or more lenses, prisms, mirrors, plates, apertures, masks, filters, phase elements, polarizers, diffractive elements, can direct radiation emanating from a treatment region 201, or a portion thereof, in response to ambient illumination or illumination by one or more radiation sources (not shown) disposed in the housing 208 onto an image capture device 203 that can form an image of the treatment region 201, or a portion thereof (e.g., area 202). The image capture device 203 can be an analog or a digital device with or without a microprocessor. The image captured by the image capture device 203 can be transmitted via an electrical or optical coupling, e.g., a cable 206, or otherwise to a display 205 mounted to the housing for viewing by a user. The image capture device 203, for example, with an integrated microprocessor, display, memory system to store the images, and battery or power supply, can be similar to those used in commercial digital photo or video cameras. The images can be magnified optically or digitally.

Figure 2B:
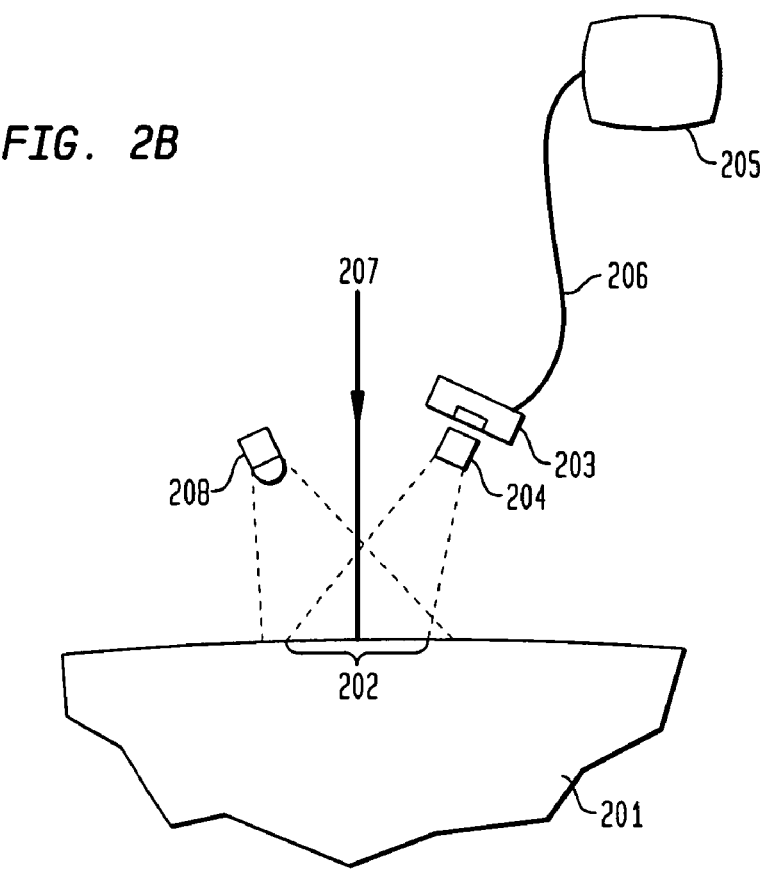

With reference to FIG. 2B, in another embodiment, in addition to the components described in FIG. 2A, a handpiece device according to the teachings of the invention can include an illumination source 208, e.g., a light source, for illuminating the treatment area, or a portion thereof, to enhance its imaging by the image capture device 203. The illumination source 208 can be any suitable light generating element, e.g., an LED, a lamp, or a laser, having a desired emission spectrum. In some embodiments, radiation from a treatment source can be employed not only for treatment but also for illumination of a target region. Further, in some embodiments, a single source can generate treatment radiation in one wavelength band and illumination radiation in another wavelength band. In some embodiments, the illumination source 208 can be pulsed and/or be synchronized with the image capturing device 203 for improved spatial and thermal resolution. The illumination source 208 can be selected to generate radiation in any desired spectral region. For example, UV, violet, blue, green, yellow light or infrared radiation (e.g., about 290–600 nm, 1400–3000 nm) can be used for visualization of superficial targets, such as vascular and pigment lesions, fine wrinkles, skin texture and pores. Blue, green, yellow, red and near IR light in a range of about 450 to about 1300 nm can be used for visualization of a target at depths up to about 1 millimeter below the skin. Near infrared light in a range of about 800 to about 1400 nm, about 1500 to about 1800 nm or in a range of about 2050 nm to about 2350 nm can be used for visualization of deeper targets (e.g., up to about 3 millimeters beneath the skin surface). Skin infrared emissions can be used for thermal imaging of the skin and/or for control of skin temperature. Although in this exemplary embodiment one illumination source 208 is utilized, it should be understood that in other embodiments the handheld device can incorporate a plurality of such sources, of the same or different emission spectra.

Figure 2C:
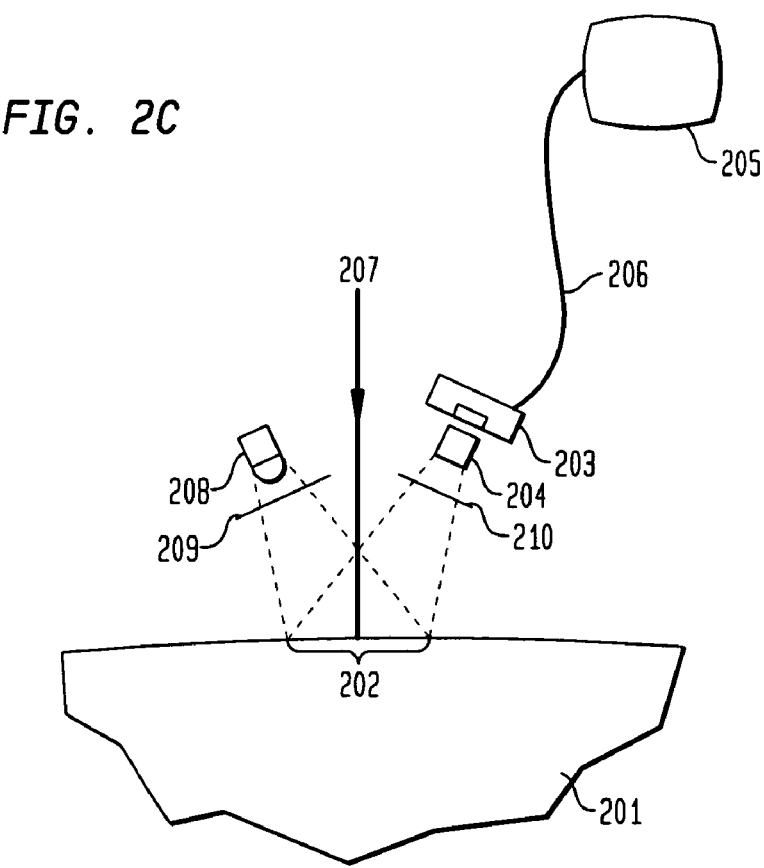

In some embodiments, a variety of optical filters and polarizing elements can be incorporated in a handpiece device of the invention to manipulate, and/or enhance, an image of the treatment area generated by the image capture device. By way of example, FIG. 2C illustrates another exemplary embodiment of a handheld device in which a pair of cross or parallel polarizers, or filters, 209 and 210 are placed, respectively, in front of the light source 208 and the optical system 204 to tailor selected parameters, e.g., the polarization and/or the spectrum, of the illumination light and/or the light reflected or emanating from the treatment area in response to the illumination light. For example, a pair of cross polarizers can be employed to suppress reflections from the surface of the treatment area 201 while capturing an image of a target region 202 located at a distance below the skin surface, as described in more detail below.

Figure 2D:
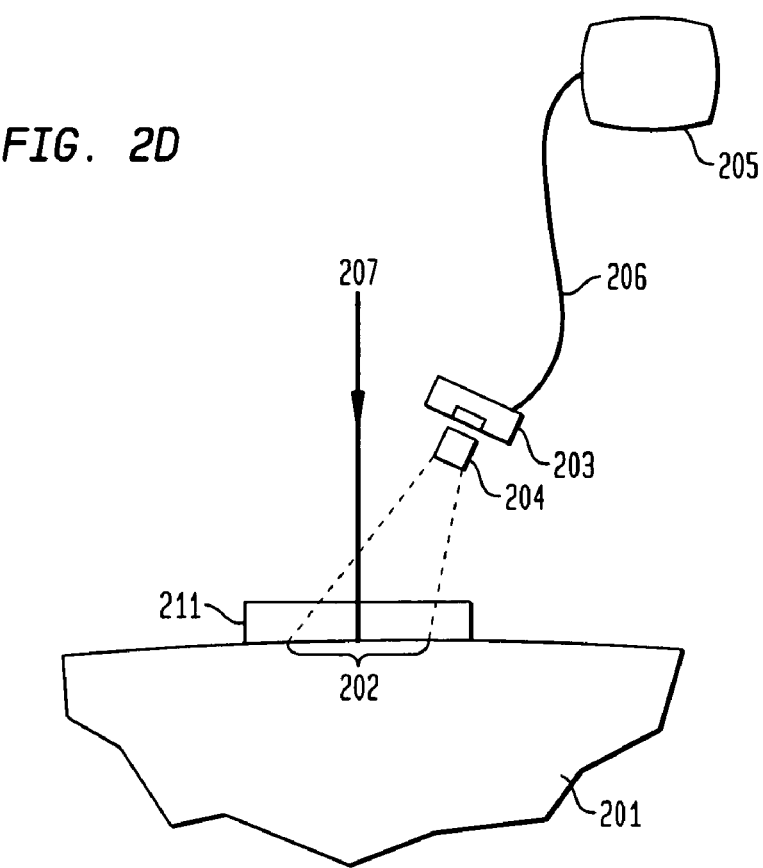

With reference to FIG. 2D, in another embodiment, a cooling or heating element 211, for example, a sapphire window, can be coupled to the proximal end of the handpiece's housing so that it can be placed in thermal contact with a portion of the patient's skin 202 during treatment in order to cool or heat the treatment area 201, or a portion thereof 202, to ensure its temperature remains within an acceptable range. In some embodiments, the element 211 can also enhance imaging of the target by improving the coupling of the illumination light into the skin and coupling the image of the target region into the image capture device. In some embodiments, a layer of a transparent lotion can be placed between the element 211 and the skin to minimize light scattering from the skin surface and reflection from the surface of the element 211 in contact with the lotion layer.

Figure 2E:
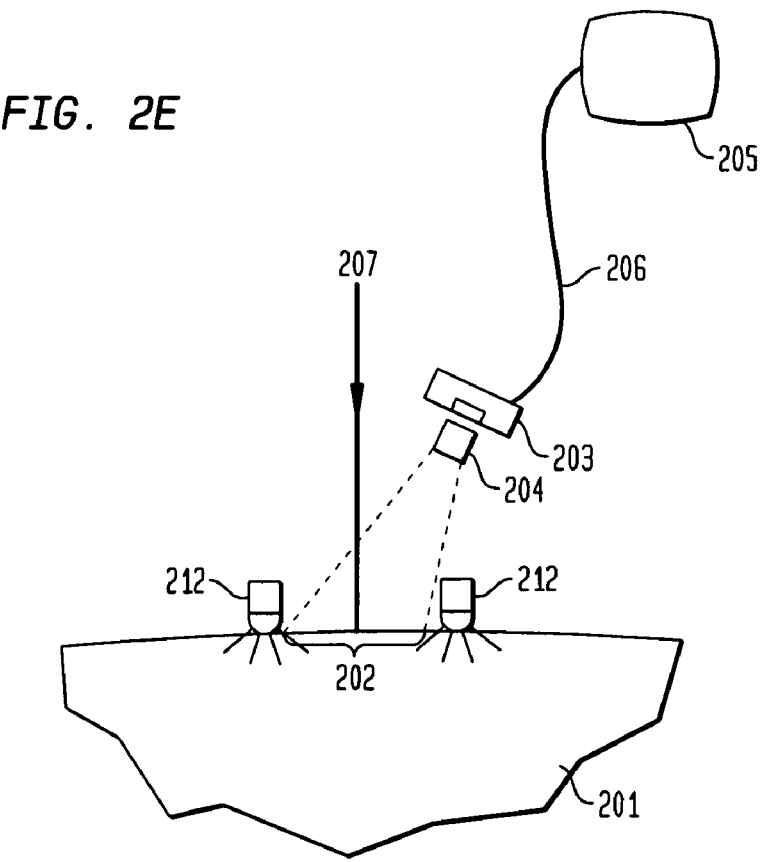

In some embodiments, a handpiece according to the teachings of the invention allows preferentially obtaining an image of a portion of a target treatment region that lies a distance below the skin surface. By way of example, in the embodiment shown schematically in FIG. 2E, two or more radiation sources 212, such as, LEDs, lamps, or lasers, that emit radiation in a desired wavelength range, e.g., in a range of about 400 to 1400 nm, or in a range of about 1500 to about 1800 nm, or in a range of about 2050 nm to about 2350 nm, can be placed around a selected target area so as to preferentially illuminate a target region under the skin surface of the target area 202 while minimizing illumination of the skin surface of the target area itself. This approach minimizes light scatter and reflection above the target region (e.g. a lesion), thus enhancing the image contrast of the target region. In some embodiments, light from an illuminator positioned on the head of a user can be used as the illumination light. Skin imaging systems can be built as optical coherent tomography systems or optical confocal microscopy systems to provide images of subsurface targets with very high resolution. In some embodiments, optical registration systems, as discussed below, can be built with decreased spatial resolution to measure average parameters of skin, such as skin pigmentation, skin redness, erythema, and/or skin birefringence.

Figure 3A:
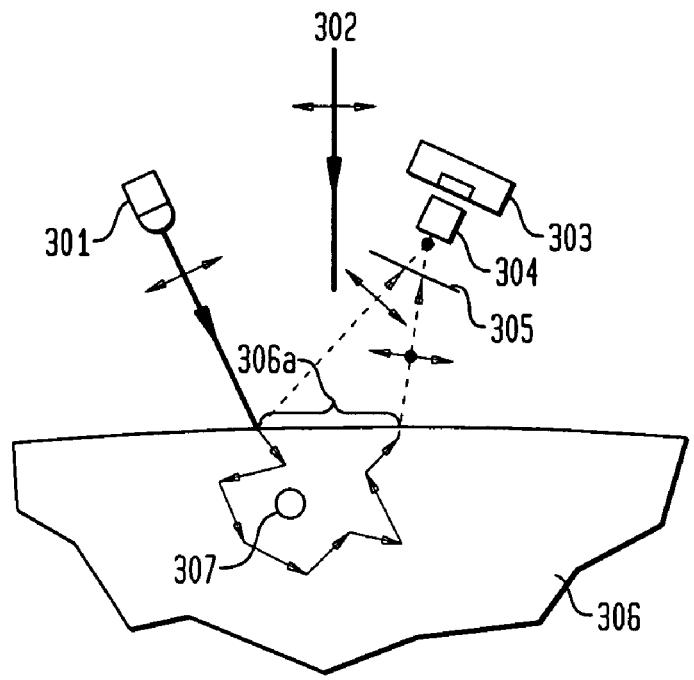

In some embodiments, a handpiece device according to the teachings of the invention is designed to preferentially provide an image of a target region 307 at a depth below the skin surface. For example, FIG. 3A schematically illustrates that a light source 301 can generate a linearly polarized beam of radiation to illuminate a target area 306a of a patient's skin 306 (alternatively, or in addition, a treatment beam 302 can be employed for illumination). A portion of the illuminating light generated by the source 301 is reflected by the skin surface of the target area towards a optical system 304 and an image capture device 303, and another portion penetrates into the skin to illuminate a target region 307 located at a depth below the skin surface. A portion of penetrated radiation leaves the patient's skin 306 after undergoing a number of scattering events to reach the optical system 304. While the light reflected from the surface of the target skin area 306 has substantially the same polarization direction as that of the illuminating light generated by the source 301, the light reaching the optical system 304 after undergoing scattering at a depth beneath the skin can include a significant polarization component in a direction perpendicular to the polarization direction of the illuminating light. In this embodiment, a cross polarizer 305 that substantially blocks light having the same polarization direction as that of the light generated by the source 301 is placed in front of the optical system 304 to prevent the light reflected directly from the skin surface from reaching the optical system 304, and hence the image capture device 303. However, the light rays scattered by the tissue at a selected depth below the skin surface have polarization components that can pass unaffected through the polarizer 305 to be imaged by optical system onto the image capture device 303. The focal plane of the optical system 304 can be adjusted to preferentially image scattered light emanating from a selected target region located at a depth below the skin surface. By way of example, polarized imaging of superficial dermis can be used for diagnostic and control of treatment of collagen using collagen birefringence.

Figure 3B:
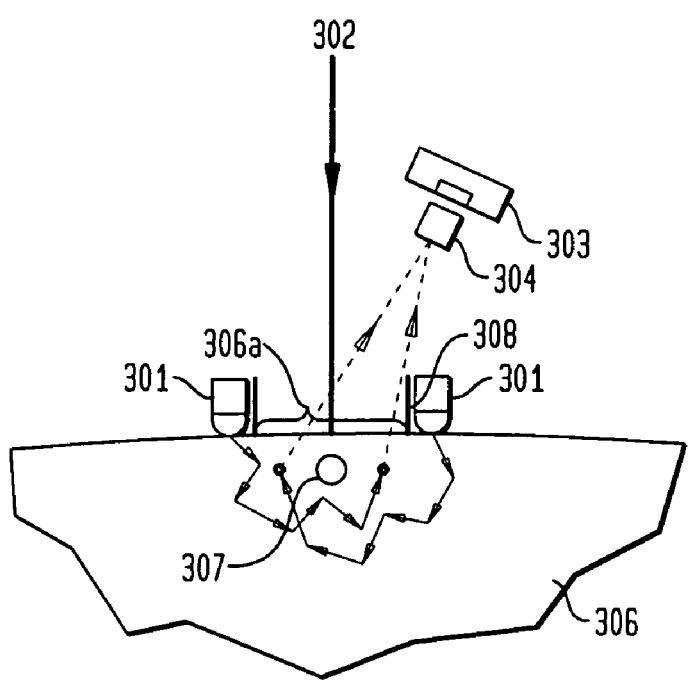

FIG. 3B schematically illustrates another embodiment of a handheld dermatological device according to the teachings of the invention that allows preferentially viewing a target treatment region disposed at a depth below the skin surface. Similar to the embodiment shown in FIG. 3A, in this embodiment, a plurality of light sources 301 surrounding a selected portion 306a of a patient's skin surface, below which a target region 307 is disposed, transmit light into the tissue below the skin surface. The transmitted light is scattered by tissue below the skin surface such that a portion of the scattered light illuminates the target region 307. Further, a portion of the light illuminating the target region 307 is reflected/scattered by tissue in the target region and finds its way, e.g., via multiple scattering events, out of the skin in a solid angle directed towards the image capture device. In addition, in this embodiment, an optical shield 308 is disposed between the light sources 301 and the portion of the skin surface below which the target region lies so as to reduce, and preferably prevent, illumination of the skin surface by photons emitted by the light sources 301. This in turn decreases, and preferably eliminates, reflection of such photons by the portion 306a of the surface of a skin portion 306 onto the image capture device, thereby enhancing the image of the buried target region. The optical shield 308 can be formed of any suitable material that is substantially, and preferably completely, opaque or reflective to photons emitted by the illumination sources 301. Such materials can include, for example, metal, plastic, and glass with special coating. Further, the shield 308 can be formed as a single unit surrounding at least a part of the perimeter of the skin surface 306, or alternatively, as a plurality of segments each disposed in proximity of the light sources 301 to shield the skin surface 306 from light emitted by that light source. In this embodiment, the image of the target is formed mostly by photons scattered from the tissue below the target (i.e., by "banana photons" as discussed in more detail below). This illumination arrangement at the same time minimizes the number of photons scattered from the tissue above the target.

In some embodiments, the optical shield 308 can also function as a mechanism for coupling a current, RF or acoustic energy into the patient's body. For example, the shield 308 can be formed as a plurality of electrodes or transducers that not only prevent photons emitted by the light sources 301 from reaching the observation area or optical system 304 but also allow coupling of a current or acoustic energy into the patient's body.

Figure 4B:
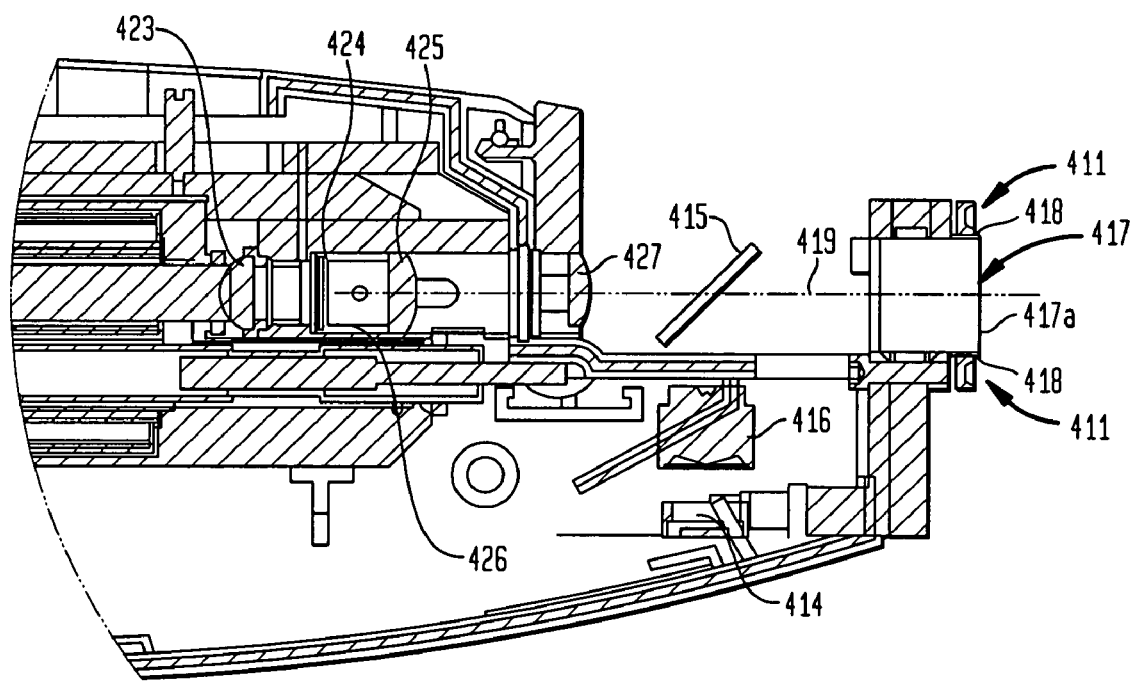
FIG. 4B is a schematic cross-sectional view of a head portion of the device of FIG. 4A, FIG. 4C schematically depicts illumination sources and a shield mounted to the head portion of the handheld device of FIGS. 4A and 4B, FIG. 5 schematically depicts an image of a skin portion obtained by an image capture device incorporated in a handheld device according to one embodiment of the invention, FIG. 6 schematically depicts illumination sources and a shield mounted to a head portion of a device according to one embodiment of the invention in which the sources provide radiation in different spectral bands.
Figure 4C:
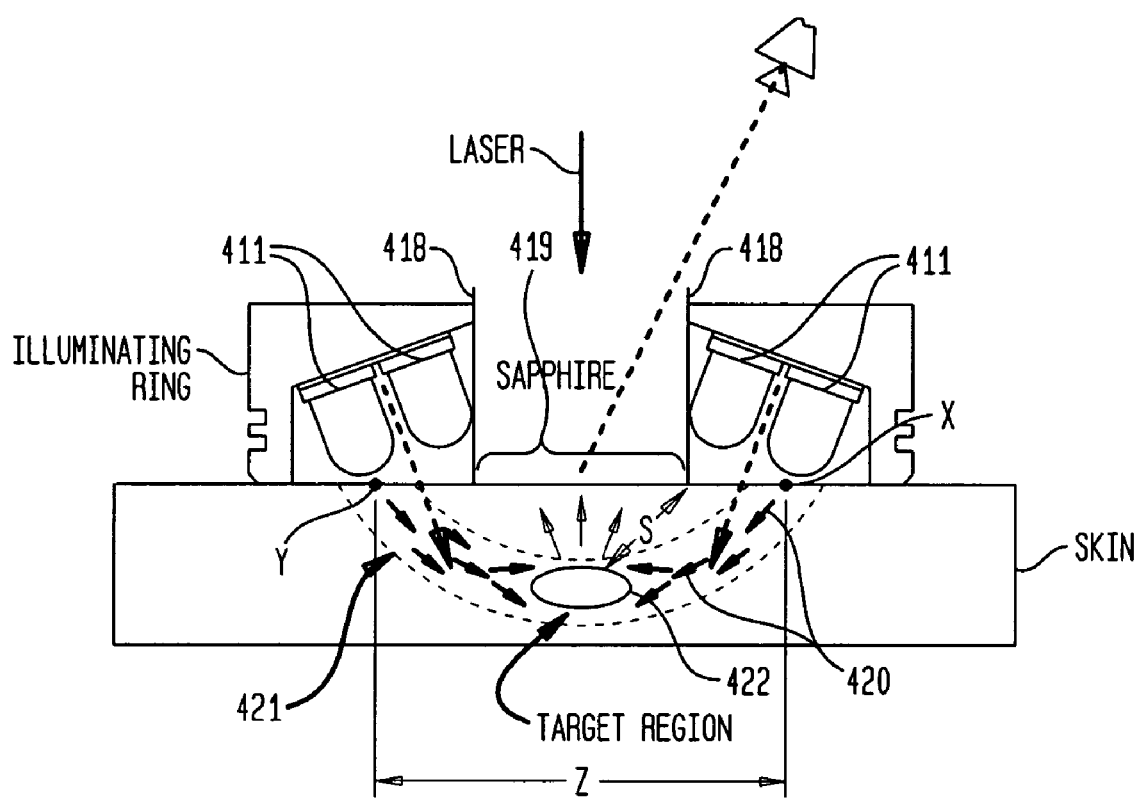
FIG. 4A is a schematic cross-sectional view of a handheld dermatological device according to one embodiment of the invention.

FIGS. 4A, 4B and 4C schematically illustrate an exemplary implementation of the target illumination system depicted in FIG. 3B incorporated in a handheld dermatological device 112 in accordance with one embodiment of the invention. A plurality of radiation-emitting sources 411 can be disposed in a head portion 412a of a housing 412 of the device in a ring, quadrant, pentagon, hexagon or any other suitable configuration. The radiation sources 411, herein also referred to as illumination or imaging radiation sources, can be utilized to illuminate a target region of a subject's skin located at a depth below the skin surface, as discussed in more detail below. A treatment radiation source 413 disposed in a body portion of the handheld device 112 generates radiation having one or more wavelengths suitable for treating a dermatological condition in the target skin region. In this exemplary embodiment, the treatment source 413 includes a neodymium (Nd) laser generating radiation having a wavelength around 1064 nm. The laser 413 includes a lasing medium 413a, e.g., in this embodiment a neodymium YAG laser rod (a YAG host crystal doped with $Nd^{+3}$ ions), and associated optics (e.g., mirrors) that are coupled to the laser rod to form an optical cavity for generating lasing radiation. In other embodiments, other laser sources, such as chromium (Cr), Ytterbium (Yt) or diode lasers, or broadband sources, e.g., lamps, can be employed for generating the treatment radiation. By way of example, the device can be employed to treat vascular lesions in depths up to about 2 millimeters with radiation having wavelengths in range of about 400 to about 1200 nm.

In some embodiment, radiation generated by the treatment source 413 can be utilized not only for treating a target region but also for illuminating that region for imaging. For example, the lasing radiation generated by the Nd:YAG laser can be employed for treatment and fluorescence radiation emitted by the laser rod can be utilized for illumination.

The illustrative handheld device 112 further includes an image capture device 414, e.g., a CCD camera, for generating an image of a target region of the subject's skin. More particularly, as discussed in more detail below, radiation reflected from a skin target region can be directed by a beam splitter 415 to a lens 416 that in turn focuses the radiation onto the image capture device 414.

A sapphire window 417 mounted at the tip of the head portion allows extracting heat from a portion of the skin surface that can be in thermal contact therewith before, during or after application of treatment radiation.

A shield 418 is mounted in the head 412 between the sapphire window and the illumination sources 411 so as to inhibit, and preferably prevent, radiation from the sources 411 from reaching a surface of a skin segment that will be in contact with a surface 417a of the window formed of sapphire or other transparent thermo conductive material, when the device is utilized for imaging and/or treating a target skin portion, as discussed in more detail below. In other words, the shield prevents radiation from the illumination sources 411 from intersecting a portion of an optical path 419 (through which treatment radiation from treatment source 413 can be transmitted to a target region and through which radiation emanating from the target region, e.g., in response to illumination by illuminating sources 411, can reach the image capture device 414) that extends through the sapphire window 417. The shield 418 is preferably formed of a material that is opaque to the radiation wavelengths generated by the illumination sources 411. Some examples of materials from which the shield 418 can be formed include, without limitation, glass, metal or plastic. In some embodiments, the internal shield surface can be coated with a material that is highly reflective to the treatment radiation to minimize heating by the treatment light, and hence minimize potential skin damage due to such heating. In addition, the reflective coating can improve the treatment efficiency by providing a photon recycling effect.

With reference to FIG. 4C, in use, the handheld device can be manually manipulated, e.g., by utilizing a handle 112a thereof (FIG. 4A), so as to place its head portion in proximity of a subject's skin surface such that the surface 417a of the sapphire window 417 is in thermal contact with a segment 419 of the skin surface. The illumination sources 411 can be activated to generate radiation that penetrates the skin surface while the shield 418 prevents this radiation from illuminating the surface of skin segment 419. As shown schematically by arrows 420, the radiation penetrating the skin is scattered by the skin tissue to illuminate a curved skin segment 421 in a portion of which a target skin region 422 is located. Due to the curved profile of the skin segment 421, the photons from the illumination sources 411 that illuminate via scattering by skin tissue are herein referred to as "banana photons." In other words, the term "banana photons" refers to those photons that propagate from one point on the skin surface (e.g., point X) to another point on the skin surface (e.g., point Y), which are separated from one another by a distance Z. The configuration of the light field generated by the banana photons is similar in shape to a banana with one end at X and the other at Y. The penetration depth of the banana photons depends on the radiation wavelength and the distance Z. A maximum penetration depth is roughly about 0.5Z. A distance S between the treatment target and the shield or the place of coupling of the illumination light into the skin can control the penetration depth of the banana photons. Deeper targets need a larger distance S. In general, the distance S is chosen to be larger that h (S>h), wherein h is a maximum depth of the target. The sources 411 can be direct LEDs, diode lasers or lamps with prelensing (as shown) or can the same sources whose light is coupled into waveguides (e.g., fibers) for directing light to the skin. More particularly, the output ends of the lens or waveguides can be optically attached to the skin for better coupling of the illumination light into the skin. In some embodiments, by direct coupling of illumination light into the skin, the shield 418 can be eliminated.

A portion of the "banana photons" illuminating the target region 422 are reflected or scattered by the skin tissue in the target region 422 into a solid angle extending to the skin surface segment 419. In other words, a portion of the "banana photons" are scattered by tissue in the target region, mostly from below the target, so as to exit the skin via the skin surface segment 419, which is shielded from direct illumination by illumination sources 411. The beam splitter 415 directs this radiation towards the image capture device 414, via the lens 416, while allowing the treatment radiation generated by the treatment source 413 to pass through and reach the skin segment 422 via the sapphire window 417. The treatment radiation can penetrate the skin to treat a dermatological condition present in the target region. The fluorescence light from the laser rod or simmer mode light from a lamp can be used for illumination. In addition, the treatment light itself can be employed for illumination to provide, for example, a better resolution of the target coagulation process during a treatment pulse.

As noted above, the shield 418 prevents the radiation generated by the illumination sources 411 from illuminating the skin surface segment 419 so as to avoid reflection of this radiation from the skin surface onto the image capture device 414, thereby maximizing the signal-to-noise ratio of the image of the target region formed by the image capture device through detection of a portion of the "banana photons" scattered by the target region.

Figure 5:
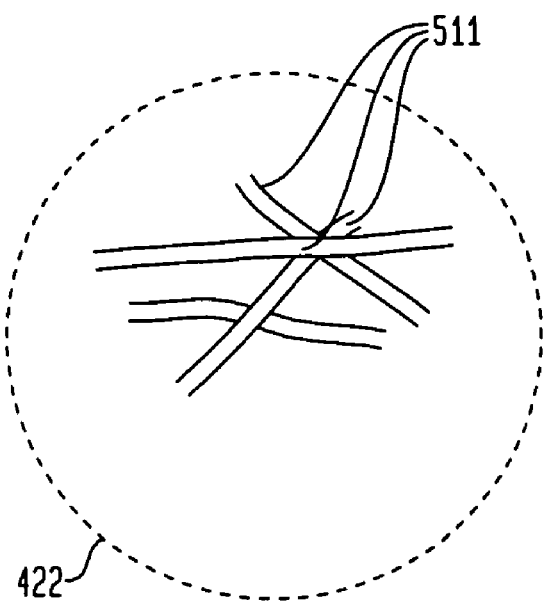

The image of the target region 422 can be utilized by an operator, e.g., a medical professional, to select a portion of the target region, or the entire target region for treatment. For example, FIG. 5 shows a schematic image of the target region illustrating a plurality of vessels 511, one or more of which it may be desired to remove.

A plurality of images can be obtained during application of treatment radiation to assess the progression of the applied treatment in real-time. Further, such images can indicate when the application of the treatment radiation should be terminated. Alternatively, subsequent to treating a target region, one or more images of that region can be obtained to determine if the applied treatment was successful. For example, a color change exhibited by a vessel under treatment can indicate whether that vessel has been coagulated in response to treatment radiation. The images can be presented to a user in a display (not shown) mounted to the housing in a manner described in connection with the above embodiments. Further, one or more images of vessels can be used to control a pressure by which the handheld device is pressed against the skin. By controlling the pressure, blood can be removed from or pumped into certain portions of the vessels to provide control of the treated vessel, thereby enhancing the treatment efficiency and preventing overtreatment. For example, for highly dense spider veins, the blood volume within the veins can be minimized before application of a treatment pulse by applying a positive pressure to prevent side effects. The treatment can be repeated several times in the same area with different pressures. Using a negative pressure, it is possible to increase the blood volume within vessels before treatment. Hence, the described image techniques can be utilized to control treatment results. Moreover, heating of the blood can result in transformation of oxy-hemoglobin into other forms that exhibit different absorption spectra (e.g., met hemoglobin). Thus, utilizing broad spectrum sources or multiwavelength sources, the temperature transformation of blood can be detected. For example, green LEDs (490–560 nm) can be used for visualization of vessels, such as leg veins or facial spider veins, before treatment while red and IR LEDs (600–670 nm, 900–1200 nm) can be used for visualization of heated blood. LED illumination in a range of about 670 nm to about 750 nm can be used to distinguish blood vessels and veins with different oxy-hemoglobin concentrations. Further, coagulation of vessels can be detected through the loss of image of the vessels due to stoppage of blood supply through the vessels or high scattering of coagulated tissue.

Referring again to FIGS. 4A and 4B, the exemplary handheld device 112 includes a zoom assembly comprising three lenses 423, 424 and 425. The lens 425 can move axially (i.e., along a direction of propagation of the treatment beam) within a slider element 426 relative to the lenses 423 and 424 so as to change the cross-sectional diameter of the treatment beam. By way of example, the cross-sectional diameter of the treatment beam can vary in a range of about 1 mm to about 15 mm.

In addition, in this exemplary embodiment, a snap-in lens 427 can be employed to augment the zoom assembly and/or to modify the cross-sectional shape of the treatment beam. For example, the lens 427 can be a cylindrical lens to impart an elliptical cross-sectional shape to the treatment beam. Other lens types can also be employed.

In some embodiments, the image capture device 414 can be a video camera for generating a movie that can show, for example, a temporal progression of an applied treatment. Providing visualization techniques in combination with treatment energy in one single device affords a user the opportunity to control a number of treatment pulses in a pulse stacking mode. For example, the device can deliver energy to a target region every 1 second (stacking mode) until coagulation of the target is completed. At this point, the user can interrupt firing of the pulses.

Figure 6:
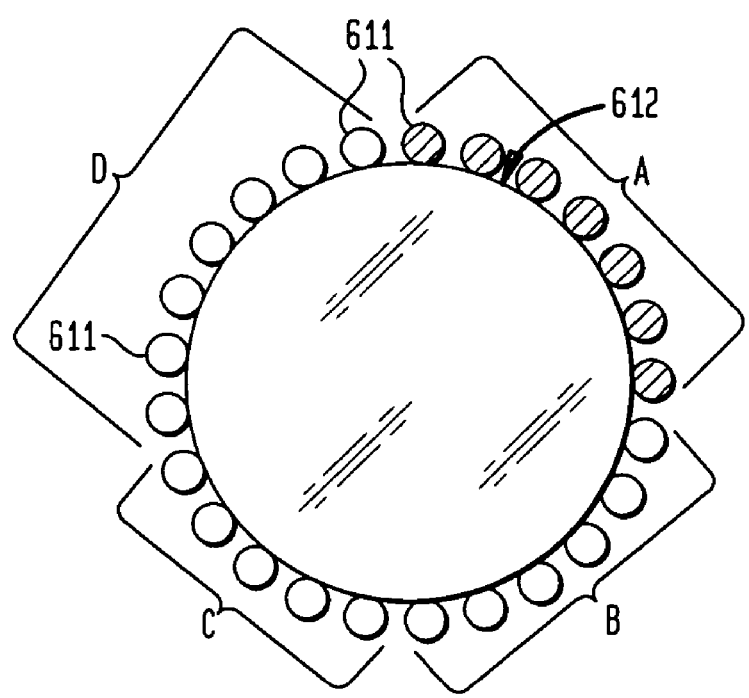

In some embodiments, the illumination sources mounted in the head portion of the handheld device can provide radiation in different spectral ranges (e.g., different colors) for illuminating a target region. For example, FIG. 6 schematically depicts a plurality of illumination radiation sources 611 mounted at a tip of a handheld device according to one embodiment of the invention and a shield 612 that prevents radiation generated by these sources from illuminating a selected skin surface segment through which an image of a target region illuminated by these sources can be obtained, in a manner described above. In this exemplary embodiment, the radiation sources in each of quadrants A, B, C and D generate radiation having one or more wavelengths different that those generated by the sources in the other quadrants. For example, while the sources in the quadrant A can provide red light, the sources in the quadrant B can generate blue light. The radiation sources in different quadrants can be activated concurrently or in succession, or in any other desired temporal pattern, to illuminate a target region. For example, the target region can be illuminated simultaneously with two or more different radiation wavelengths (e.g., two different colors). Alternatively, the target region can be illuminated by sources generating radiation with the same spectral components at a time (e.g., one color at a time). In this manner, images of the target region illuminated by different radiation wavelengths can be obtained. In some embodiments, one or more of the illumination sources can generate radiation in two or more wavelength bands.

Figure 7:
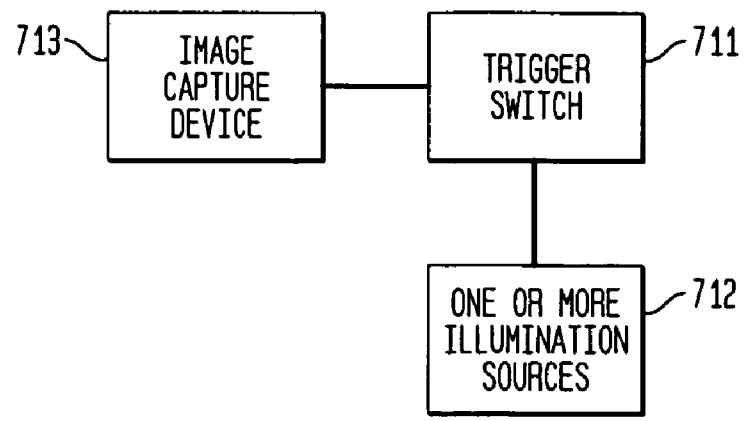
FIG. 7 is a diagram depicting a control system for selective activation of illumination sources and/or an image capture device incorporated in a handheld device according to one embodiment of the invention, FIG. 8 schematically depicts a handheld device according to one embodiment of the invention having a CCD camera and an image processor for processing images acquired by the camera, FIG. 9 schematically depicts a handheld device having a communications module for transmitting images obtained by an image capture device incorporated in the handheld device to an external computing system, via wire or wireless communication, FIG. 10 schematically depicts an image of a target region presented in a display of a handheld device according to one embodiment of the invention in which a graphical object in employed to show a cross-section of a treatment beam, FIG. 11A schematically illustrates a handheld device according to one embodiment of the invention in which a command menu can be presented to a user, FIG. 11B schematically illustrates a handheld device according to another embodiment having a microprocessor in communication with an image capture device to process images acquired by the device so as to identify occurrence of a selected condition, such as completion of a treatment protocol, FIG. 12 schematically illustrates tracking the position of a marker identifying the location of a selected site in two images, which are shifted relative to one another, FIG. 13A schematically illustrates a handheld device according to another embodiment of the invention having a radiating guiding element and an illumination source coupled to the guiding element so as to generate refractively coupled illumination waves for illuminating a subsurface skin region and an image capture device for generating an image of that region, FIG. 13B schematically illustrates the device of FIG. 13A in which total internal reflection at an contact surface of the guiding element and the skin surface is employed for visualizing the skin surface, FIG. 14A schematically illustrates a device according to one embodiment of the invention having an array of sensors for generating a dielectric image of a skin portion and a display for displaying that image, FIG. 14B schematically illustrates a device according to one embodiment of the invention that includes, in addition to sensors for generating a dielectric image of a skin portion and a display for displaying that image, one or more transducer elements for applying energy to the skin.

In some embodiments, the image capture device can be activated in synchrony with activation of one or more radiation sources utilized for illuminating a skin target region. By way of example, the image capture device can be activated to acquire an image of the target region each time the illumination sources in one of the quadrants (FIG. 6) are triggered. For example, with reference to FIG. 7, the handheld device can include a control unit (e.g., a triggering switch) 711 for sending concurrent triggering signals to selected ones of the illumination radiation sources 712 mounted on the device and an image capture device 713. Alternatively, one trigger signal can be delayed relative to another by a selected time duration. For example, the triggering signal activating the image capture device can be delayed relative to that activating one or more of the radiation sources.

Figure 8:
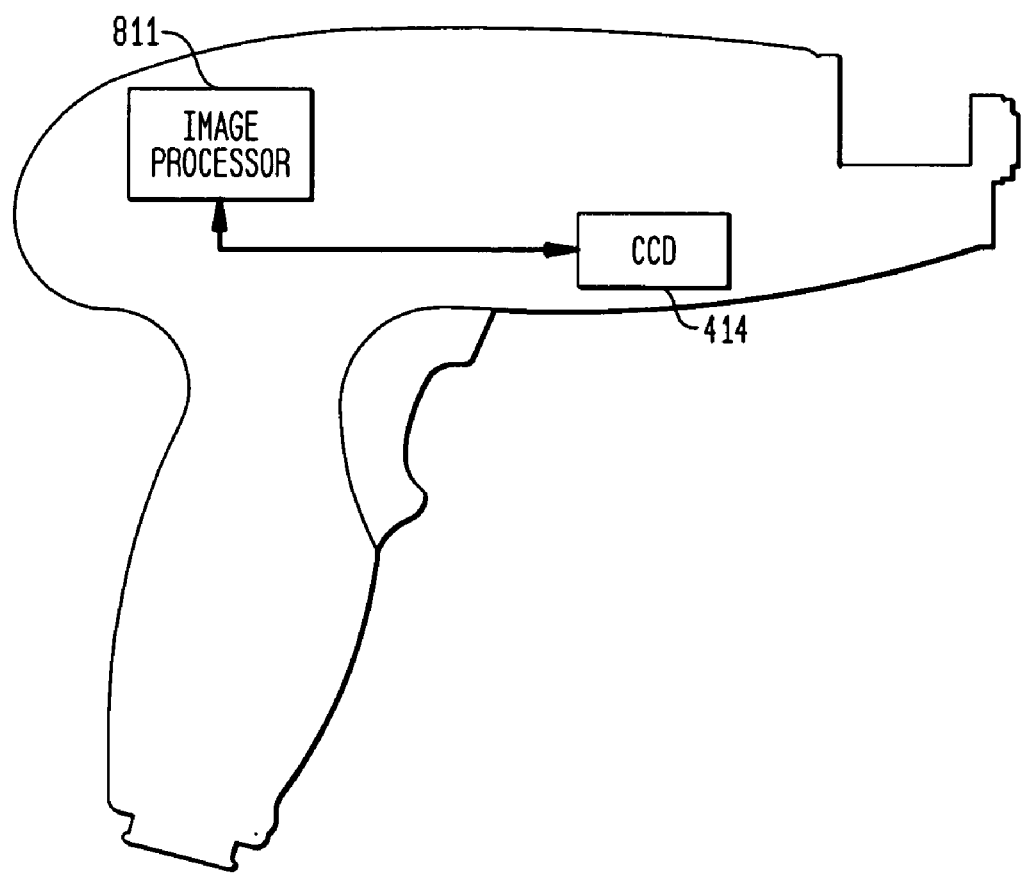

With reference to FIG. 8, in some embodiments, the processing of the images can be achieved by an microprocessor 811 incorporated in the handheld device that is in communication with the image capture device 414.

Figure 9:
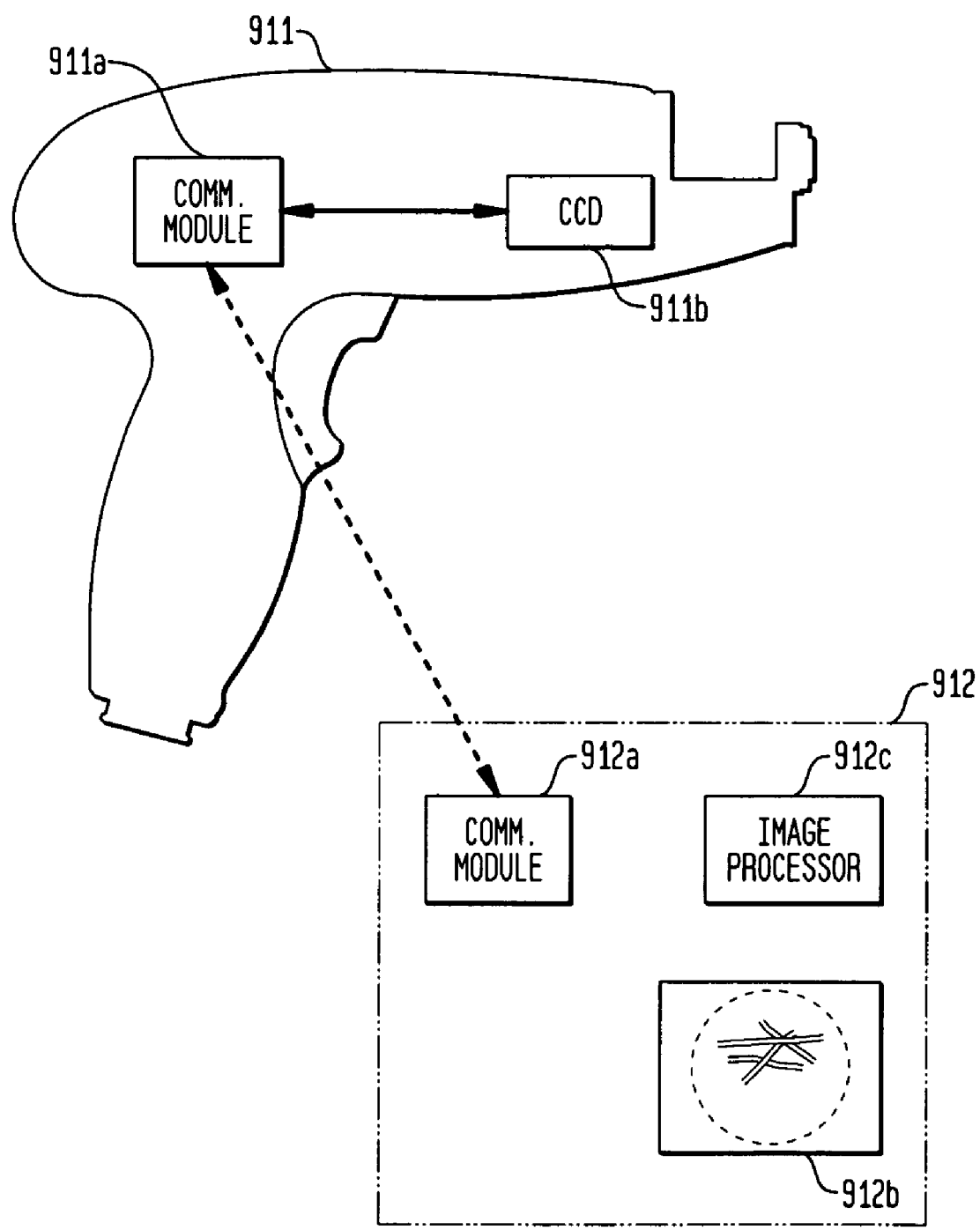

Alternatively, with reference to FIG. 9, the images can be transferred from a handheld device 911 according to one embodiment of the invention to a separate computing device 912 on which appropriate software for image construction can be executed. For example, in some embodiments, images of a target skin region acquired by the handheld device can be transmitted by employing, for example, a wireless protocol to the computing device 912, which can be remotely located relative to the handheld device. For example, the handheld device can include a communications module 911*a* for transmitting images acquired by an image capture device 911*b* to the computing device 912, via a corresponding communication module 912*a* of the computing device. The computer 912 can include a display 912*b* for displaying the images to a user, e.g., a medical professional. Further, the computer 912 can optionally include an image processing module 912*c* for processing the images of the target region.

In some embodiments, the image of the target region can be analyzed by employing image recognition techniques to extract selected features, e.g., vascular legions. These extracted features can be displayed on a display mounted to the handheld device, such as a display similar to that shown above in FIG. 1A in connection with the handheld device 101.

Figure 10:
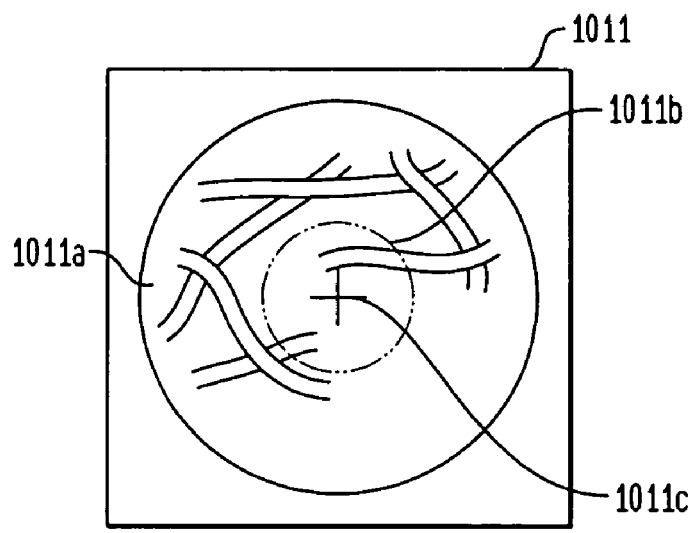
Figure 11A:
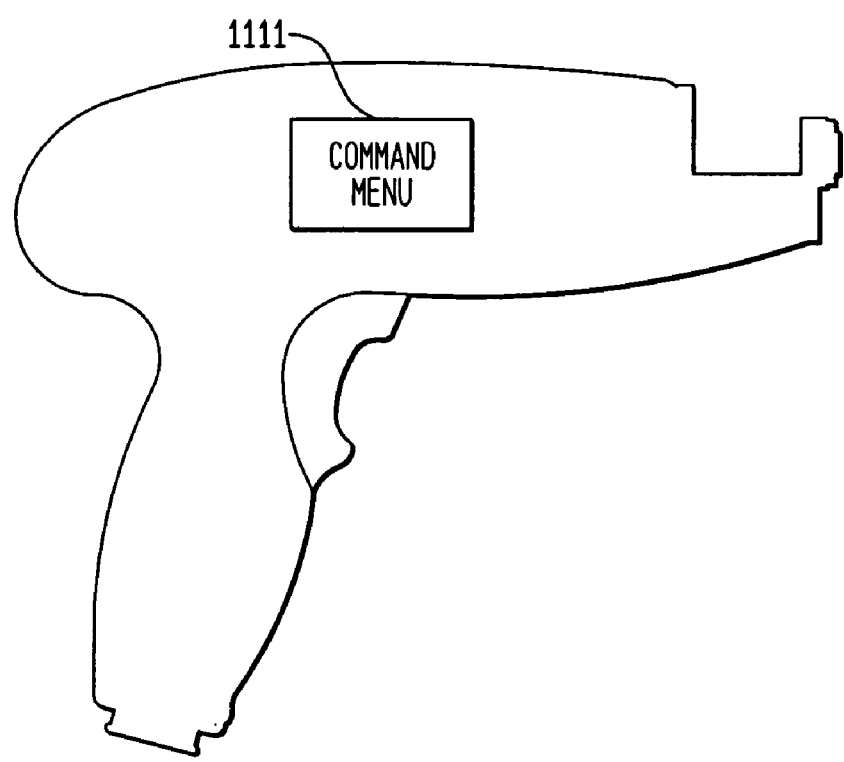

With reference to FIG. 10, in some embodiments, a display unit 1011 of a handheld device according to one embodiment of the invention can present not only an image 1011*a* of a target skin region but also a graphical element 1011*b*, e.g., a circle, that schematically depicts the cross-section of the treatment beam relative to the target region. In some embodiments, the user can select the portion of the target region identified by the graphical element 1011*b*, e.g., the portion circumscribed by the circle, for magnified viewing. For example, with reference to FIG. 11, the handheld device can provide a menu 1111 to a user in a portion of the display utilized for displaying images, or in a separate display, that can be navigated to select commands for controlling selected display characteristics of the image of the target region. For example, the menu can provide commands for magnifying the portions of the image associated with a portion of the target region to which treatment radiation is being applied. Such magnification can be achieved, for example, automatically in response to the user's selection by sending appropriate signals to a zoom lens system of the handheld device, such as the zoom lens assembly shown in the above handheld device 112 (FIG. 4A). For example, a piezoelectric element electrically coupled to a movable lens of a zoom lens assembly can be activated in response to the user's selection to move that lens, thereby modifying the magnification of the displayed image of the target region.

The graphical elements suitable for displaying the position of a treatment beam relative to an image of a target region are not limited to that described above. For example, referring again to FIG. 10, a cross-hair 1011*c* can be employed to denote the center of the treatment beam's cross section. Such visual aids facilitate positioning of the handheld device relative to a patient's skin so as to more effectively apply treatment radiation to a portion of a target region whose image is displayed. These alignment features can significantly increase efficacy and safety of the treatment. For example, in the absence of such features, it is difficult to position small treatment beams (e.g., spot size less than 3 mm) on small treatment targets, such as vessels.

Figure 11B:
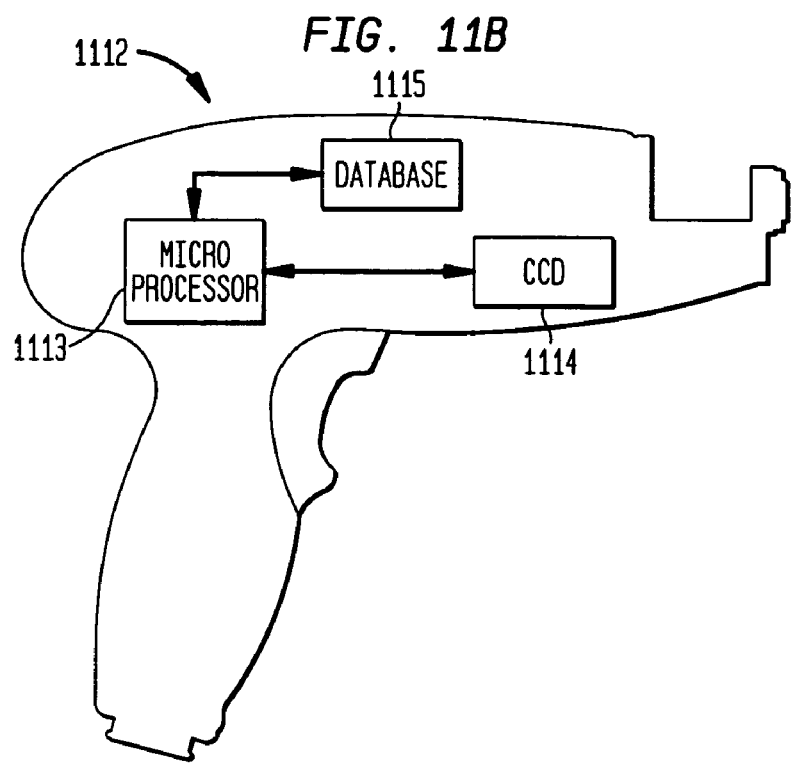

With reference to FIG. 11B, a handheld device 1112 according to one embodiment of the invention can include a microprocessor 1113 electrically, or optically or via a wireless connection, coupled to an image capture device 1114 to receive images acquired by the image capture device. The microprocessor can utilize these images to monitor an applied treatment. For example, the microprocessor can be programmed to compare changes in selected parameters of the skin tissue (e.g., color of a vessel) extracted from the acquired images with threshold values for these parameters stored, for example, in a database 1115. The database can be maintained in the handheld device, or alternatively, the needed data can be downloaded to the device from a remote database. By way of example, comparison of color of a vessel, pigment lesion, tattoo irradiated to cause its coagulation can signal that the treatment has been successful. Upon detecting threshold values for one or more selected parameters, the microprocessor can alert a user, e.g., by providing a visual or audible signal, that the parameters have reached the preset threshold values. The threshold values can signal, for example, completion of a treatment protocol, or onset of an undesirable condition, e.g., the temperature of skin exceeding a threshold value.

Figure 12:
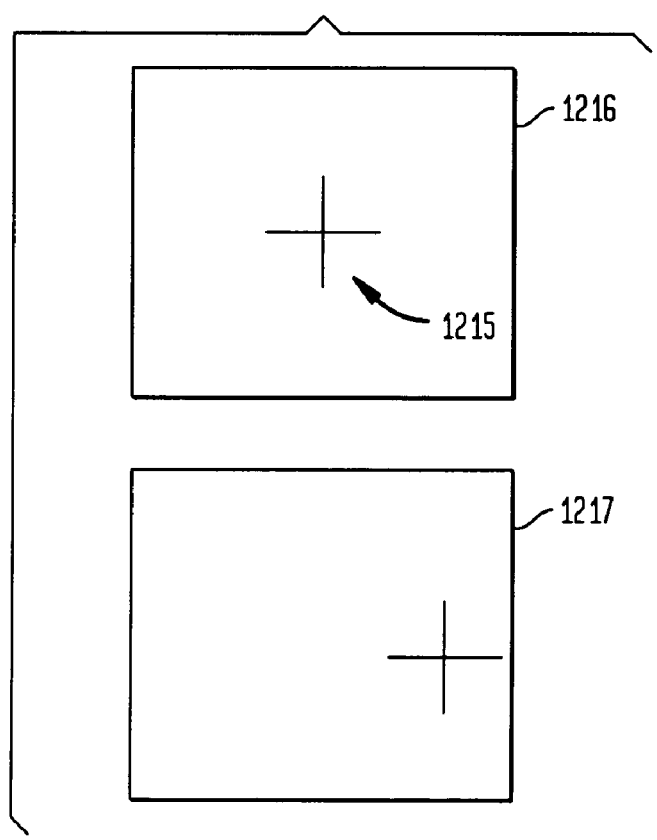

In some embodiments, the handheld device can track the position of a target region, e.g., a treatment site, which can be identified by a marker in an image, from one image to the next. For example, with reference to FIG. 12, a marker 1215 is provided on an image 1216 of a target skin region to identify a selected site, e.g., a treatment site. A subsequent image 1217 may obtained such that it is shifted relative to the image 1216 (for example, a result of movement of the handheld device). In these embodiments, the position of the marker is tracked such that it can be presented at the appropriate location of the image 1217 identifying the selected site in the new image. Such tracking can be particularly advantageous when one image is shifted relative to a subsequent image, for example, as a result of motion of the handheld device. More specifically, in some embodiments, the microprocessor can implement an algorithm by which a marker placed on one image to identify a selected site (e.g., the treatment site) is transferred to a subsequent image while taking in account the motion of the image capture device between acquisition of the two images.

In one exemplary tracking algorithm, the motion of an image pixel can be modeled as a combination of translation in the image plane (herein referred to as x-y plane) and rotation about an axis perpendicular to this plane. The following notations are employed in describing the algorithm: x, y denote a pixel coordinates, Vx, Vy velocity components of a pixel along the x and y coordinates; Ux, Uy indicate components of translation velocity (the same for all pixels in each image but may vary from one image to another); Rx, Ry denote the coordinates of the center of rotation at which the rotation axis cross the x-y plane (all pixels in each image rotate around the same center but the center may vary from one image to another); and ω denotes the angular velocity of rotation. An optical flow model of the pixels can then be described by the following relations:

$$Vx = Ux - \omega \cdot (y - Ry),$$

$$Vy = Uy + \omega \cdot (x - Rx). \tag{1}$$

The above equations can be cast in a linear format by introducing variables $X_1$, $X_2$ and $X_3$ defined as follows:

$$X_1 = Ux + \omega \cdot Ry, \quad X_2 = Uy - \omega \cdot Rx, \quad X_3 = \omega. \quad (2)$$

More specifically equations (1) take the following form when the variables $X_1$, $X_2$ and $X_3$ are employed:

$$Vx = X_1 - y \cdot X_3,$$

$$Vy = X_2 + x \cdot X_3. \quad (3)$$

The following optical flow constraint equation can be utilized to determine the change in the position of a pixel between images:

$$Vx \cdot \frac{\partial I}{\partial x} + Vy \cdot \frac{\partial I}{\partial y} = -\frac{\partial I}{\partial t}. \quad (4)$$

wherein $I(x,y,t)$ represents the pixel brightness at a location $(x,y)$ in an image at a time t. Utilizing the notations Ix, Iy and It for the derivatives in equation (4) and substituting values for Vx and Vy defined by equations (3) into equation 4, the following equation is yielded:

$$Ix \cdot X_1 + Iy \cdot X_2 + (x \cdot Iy - y \cdot Ix) \cdot X_3 = -It. \quad (5)$$

The above equation (5) should be valid for every point of an image. When a region of the image represented by several pixels is selected, a system of equations can be obtained, which can be defined as follows:

$$Ix_k \cdot X_1 + Iy_k \cdot X_2 + (x_k \cdot Iy_k - y_k \cdot Ix_k) \cdot X_3 = -It_k, \quad (6)$$

wherein the index k=1, 2, . . . n can represent the point number.

The coefficients of $X_1$, $X_2$ and $X_3$ in the above set of equations can be represented by the following matrix:

$$A = \begin{bmatrix} Ix_1 & Iy_1 & x_1 \cdot Iy_1 - y_1 \cdot Ix_1 \\ Ix_2 & Iy_2 & x_2 \cdot Iy_2 - y_2 \cdot Ix_2 \\ \cdots & \cdots & \cdots \end{bmatrix}. \quad (7)$$

By way of example, if the number of points (n) is selected to be three (n=3), then A is a square matrix, and the values of $X_1$, $X_2$ and $X_3$ can be obtained by utilizing the following relation:

$$\begin{bmatrix} X_1 \\ X_2 \\ X_3 \end{bmatrix} = -A^{-1} \cdot \begin{bmatrix} It_1 \\ It_2 \\ It_3 \end{bmatrix}. \quad (8)$$

where $A^{-1}$ is the inverse of the matrix A.

In many embodiments of the invention, the number of points is chosen to be much larger than 3 so that the matrix A is not square and the system of equations (6) is redundant. Utilizing the least square criteria, the following solution can be obtained:

$$\begin{bmatrix} X_1 \\ X_2 \\ X_3 \end{bmatrix} = -(A^T \cdot A)^{-1} \cdot A^T \cdot \begin{bmatrix} It_1 \\ \cdots \\ It_n \end{bmatrix}. \quad (9)$$

The algorithm for tracking a marker initially positioned at $x_m, y_m$ in a first image can then include the steps of choosing a number of points (preferably larger than 3) in a central portion of the first image and evaluating derivatives $Ix_k$, $Iy_k$ at these points to generate the matrix A. In many embodiments, the determinant of the matrix $A^T A$ is calculated to ensure that it is not too small. If the determinant is too small, additional points can be selected and the matrix A regenerated. Using the first image and a second image, the time derivative $It_k$ are evaluated at the selected points (e.g., by assuming dt=1). The above relation (9) is then employed to evaluate $X_1$, $X_2$ and $X_3$. The values of Vx and Vy are evaluated at the marker position ($x=x_m$, $y=y_m$). The marker position in the second image can then be determined as follows: $x_m \to x_m - Vx \cdot dt$, $y_m \to y_m - Vy \cdot dt$; dt=1. The above steps can be repeated for the subsequent images.

Figure 13A:
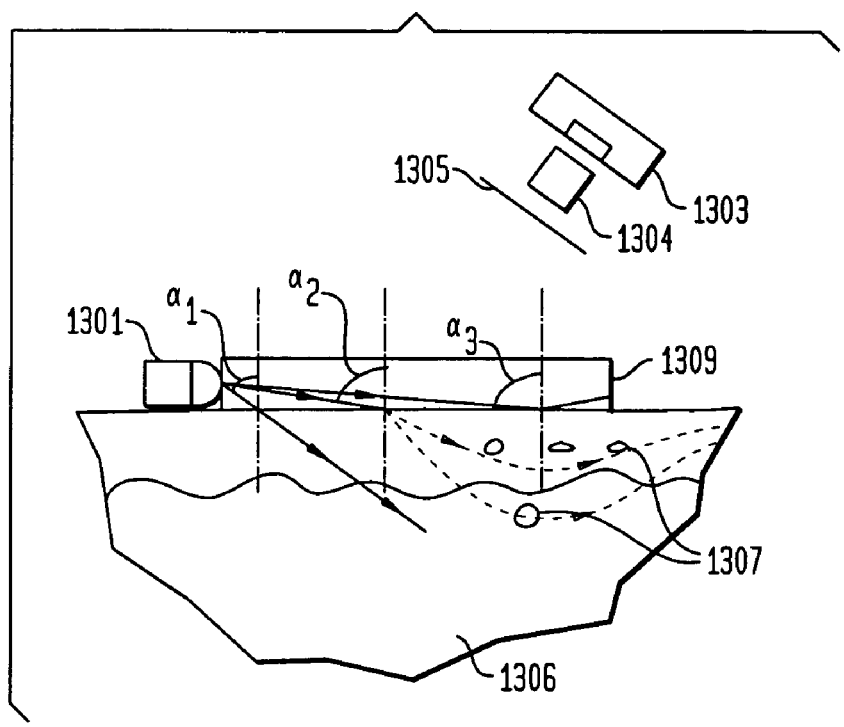

With reference to FIG. 13A, in another embodiment, refractive illumination waves, or evanescent waves, traveling at an interface of an optical element 1309 and the surface of an observation area of a patient's skin can be employed to illuminate a skin surface or a thin subsurface layer of the skin for imaging thereof by an image capture device 1303. This embodiment can be used for precise imaging and control of skin surface conditions, for example, stratum corneum structure, pore size, sebaceous follicle opening, hair follicle opening, skin texture, wrinkles, psoriasis. More particularly, the optical element 1309, which is disposed over the observation area, is selected to be substantially transparent to radiation emitted by the light source 1301, which is optically coupled to the element 1309. By control of refractive index of the guiding element and incident angle of the illumination radiation at the skin contact surface of the guiding element, imaging contrast of a visualized target can be enhanced. The light source 1301 can illuminate the optical guidance element 1309 from a side surface thereof. A portion of the light entering the optical element 1309 is totally internally reflected at the interface of the optical element and the patient's skin or partly penetrates into the skin at a control angle while generating refractive coupled illumination light waves traveling along the interface as surface or waveguide electromagnetic waves that penetrate to a depth of the patient's skin. Such refractive coupled illumination waves can illuminate a subsurface region of the patient's skin, e.g., stratum corneum, epidermis or a top portion of the dermis up to 300 microns depth. Depth of penetrations into the skin depends on the illumination wavelength, angle of incidence as, the refractive index of the coupling element 1309 ($n_1$) and effective refractive indices of skin layers, such as stratum corneum ($n_2$), epidermis ($n_3$), upper dermis ($n_4$) and deep dermis ($n_5$), where $n_2 > n_3 > n_4 > n_5$. A portion of the refractively coupled illumination light is scattered by the target 1307. The scattered light can then be focused by the optical system 1304 onto the image capture device 1303 to generate an image of the subsurface region. The contrast of the target image is maximized as the skin structures below the target cause minimal scattering light noise. The refractive coupling of the illumination wave can be optimized for different depths of penetration or for maximum skin resolution. For example, if an incident angle ($\alpha_1$) is less than $\arcsin(n_2/n_1)$ ($\alpha_1 < \arcsin(n_2/n_1)$), the illumination light can penetrate into the skin.

Figure 13B:
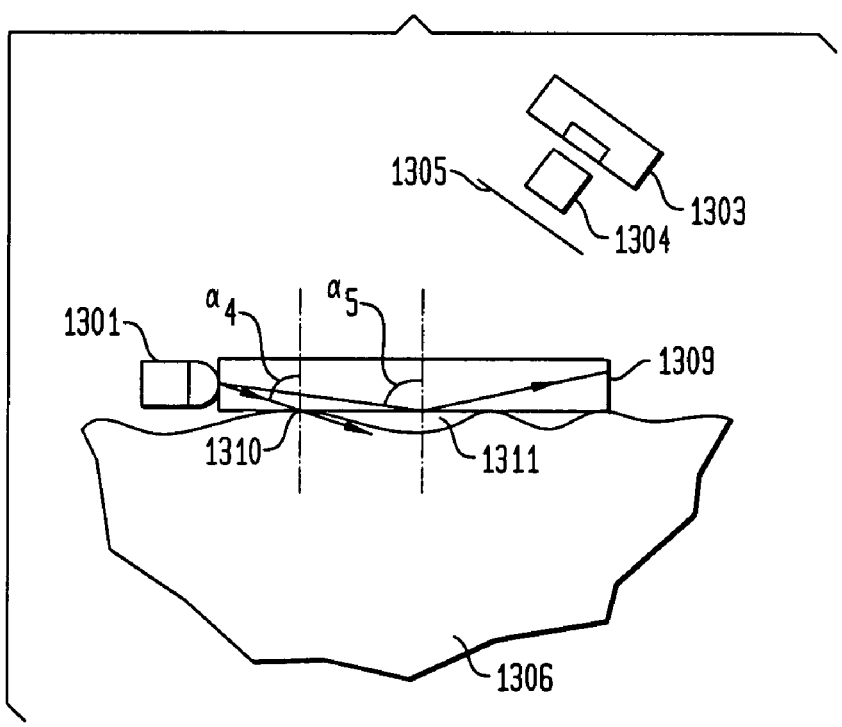

If $\arcsin(n_3/n_1) < \alpha_2 < \arcsin(n_2/n_1)$, the illumination wave propagates mostly into stratum coreum. If $\arcsin(n_4/n_1) < \alpha_2 < \arcsin(n_2/n_1)$, the illumination wave propagates mostly into epidermis and stratum corneum. If $\arcsin(n_5/n_1) < \alpha_2 < \arcsin(n_2/n_1)$, the illumination wave propagate mostly into upper dermis, epidermis and stratum corneum. These conditions are applicable for wavelengths with low absorption and scattering in the skin bulk (500–1400 nm, 1500–1800 nm). If $\alpha_3 > \arcsin(n_2/n_1)$, the illuminating light totally internally reflects from contact surface of coupling element 1309. In this case, an image on imaging capture device 1303 looks like uniform field and can not be used for subsurface target visualization. However, this condition can be very effective for obtaining high contrast image of skin surface. For example, with reference to FIG. 13B, the total internal reflection mode can be used for visualization of skin surface irregularities, holes in stratum corneum, distribution on the skin surface of sebum, bacteria, water, oil, pores, glands and follicles opening. If $\alpha_4 < \arcsin(n_2/n_1)$, the illumination light penetrate into the skin and this contact area 1310 is imaged on 1303 as bright or a black spot, depending on the initial adjustment of the image capture device. But if $\arcsin(n_6/n_1) < \alpha$, where $n_6$ is reactive index of air in the gap 1311 or lotion which fills this gap, the illumination light totally reflects from the contact surface and 1311 is invisible to the image capture devise 1303. As a result, a skin texture image can be acquired by the image capture device 1303.

In other embodiments, the total internal reflection from a contact surface of the element 1309 with the skin can be interrupted by a material on the skin having a high absorption coefficient at the illumination wavelengths. For example, for detection of water distribution on the skin surface, radiation with wavelengths around 1450, 1900 or 2940 nm can be used. Further, wavelengths corresponding to the peaks of lipid absorption can be employed for visualization of oil or sebum distribution on the skin. By way of example, this embodiment can be used for control of topical drug or lotion distribution on the skin.

Further, a lotion (not shown) can be applied to the skin surface 1306 below the optical element 1309. The lotion's refractive index can be selected to adjust the penetration depth of photons illuminating the subsurface region, thereby controlling the depth of observation. The use of refractively coupled illumination waves for imaging shallow subsurface regions of a patient's skin can provide certain advantages. For example, the evanescent waves, which exponentially decay within the skin, can effectively illuminate a selected subsurface region of interest and not deeper regions. This selective illumination advantageously enhances signal-to-noise ratio of an image generated by capturing photons reflected from the skin in response to illumination.

The above exemplary system in which refractively coupled illumination waves are employed to image subsurface skin regions can be incorporated in a handheld device according to one embodiment of the invention. In some cases, the optical guidance element 1309, in addition to facilitating generation of illumination subsurface waves, or evanescent waves, can also extract heat from the skin portion with which it is in thermal contact.

Figure 14A:
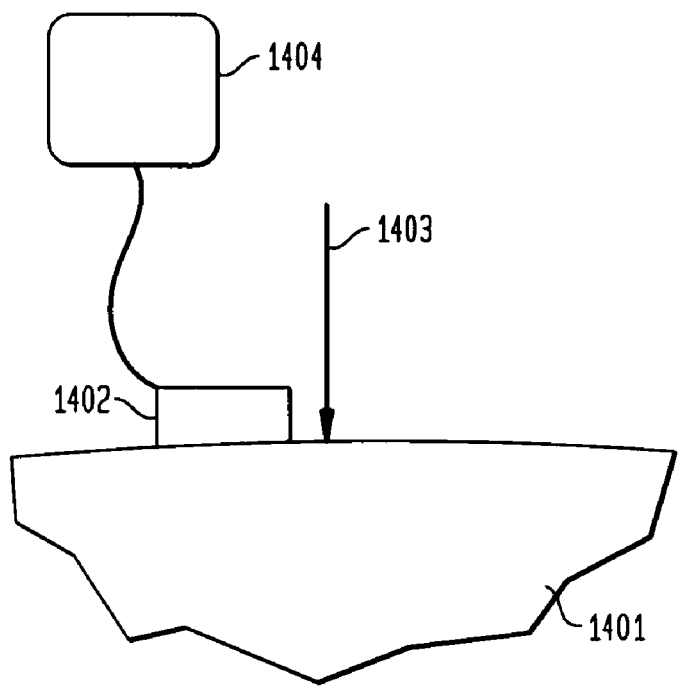

With reference to FIG. 14A, in some embodiments, the handheld device can include an array of capacitive, piezo and/or optical sensors 1402 that can be coupled to a target treatment area to provide information regarding selected properties thereof. For example, an array of capacitive sensors can be employed to generate a dielectric image of the treatment area before, during and/or after irradiation of the target area 1401 by a beam 1403 of electromagnetic radiation or any other suitable energy source. For example, capacitive touch sensors marketed by Orient Drive, Inc. of Mountain View, Calif. under the trade designation MMF200-0D1-01 can be utilized for this purpose. This sensor is marketed as an integrated ASIC having a processor as well as SRAM and flash memory. Other sensors that do not include integrated processor and/or memory can also be utilized in the practice of the invention. The resolution of the sensors can be selected to be sufficiently high to distinguish a treatment target, e.g., a vein, from its surrounding area. The data obtained by the sensor array can be transmitted to a display 1405 mounted to the device's housing for presentation to a user in a selected format. For example, the display can present dielectric data as a false color image in which each color hue represents a measured value of dielectric constant.

Figure 14B:
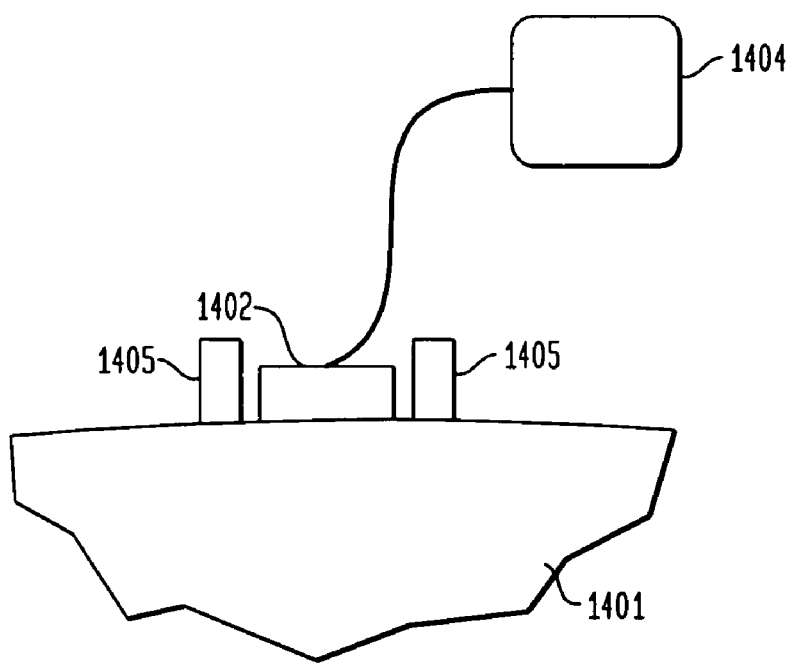

With reference to FIG. 14B, in another embodiment, a diagnostic/therapeutic dermatological handheld device according to the teachings of the invention can include, in addition to an array of capacitive, piezo or optical sensors 1402 coupled to a display, a plurality of electrodes or transducers 1405 that can be disposed in proximity of a selected target area so as to couple an electrical current or acoustic energy into the patient's body 1401. Optical sensor 1402 in this embodiment can be built as a confocal microscope or an optical coherent tomography head.

Figure 15:
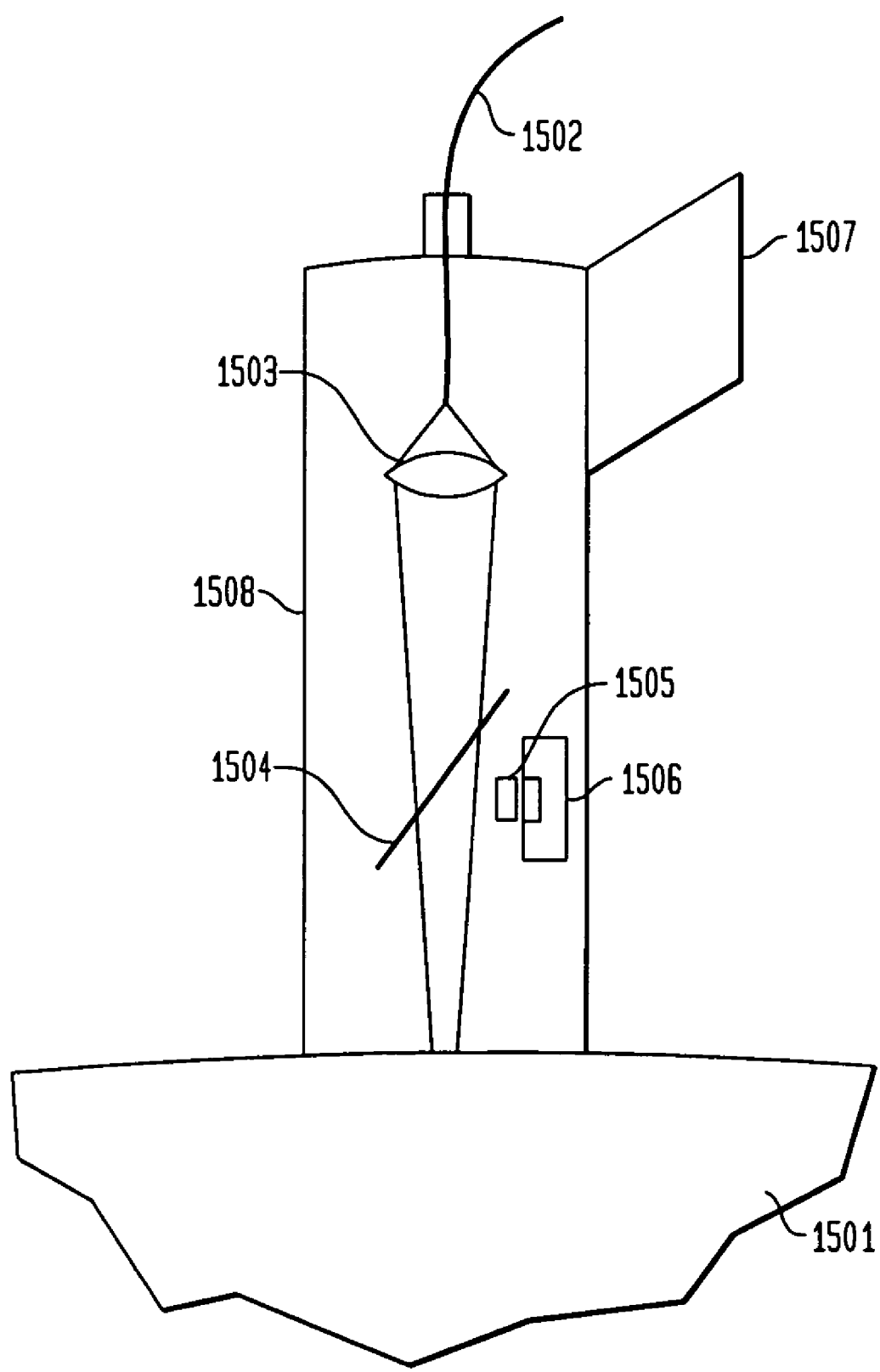
FIG. 15 is a schematic cross-sectional view of a handpiece dermatological device according to one embodiment of the invention having a housing to which a waveguide is coupled to transmit energy from a remote source to a skin portion.

FIG. 15 schematically depicts a cross-sectional view of a handpiece dermatological device according to the teachings of the invention that includes a housing 1508 into which a waveguide 1502, for example, an optical fiber, is coupled to transmit energy, e.g., electromagnetic energy, from a source (not shown), e.g., a source remotely located from the device, to the handpiece for delivery onto a treatment area 1501. In this embodiment, the waveguide 1502 is an optical fiber that is optically coupled to a lens that focuses light delivered by the fiber onto a selected treatment area. A beam splitter 1504 allows the light directed by the lens 1503 towards the treatment area 1501 to pass through while it diverts a portion of light reflected from the treatment area, either in response to illumination by the treatment beam or ambient illumination, or in response to illumination by a separate light source, to an image capture device 1506 via an optical system 1505. The image capture device 1506 in turn generates an image of the treatment area, or a portion thereof, and transmits the image to a display 1507 for viewing by a user.

Figure 16A:
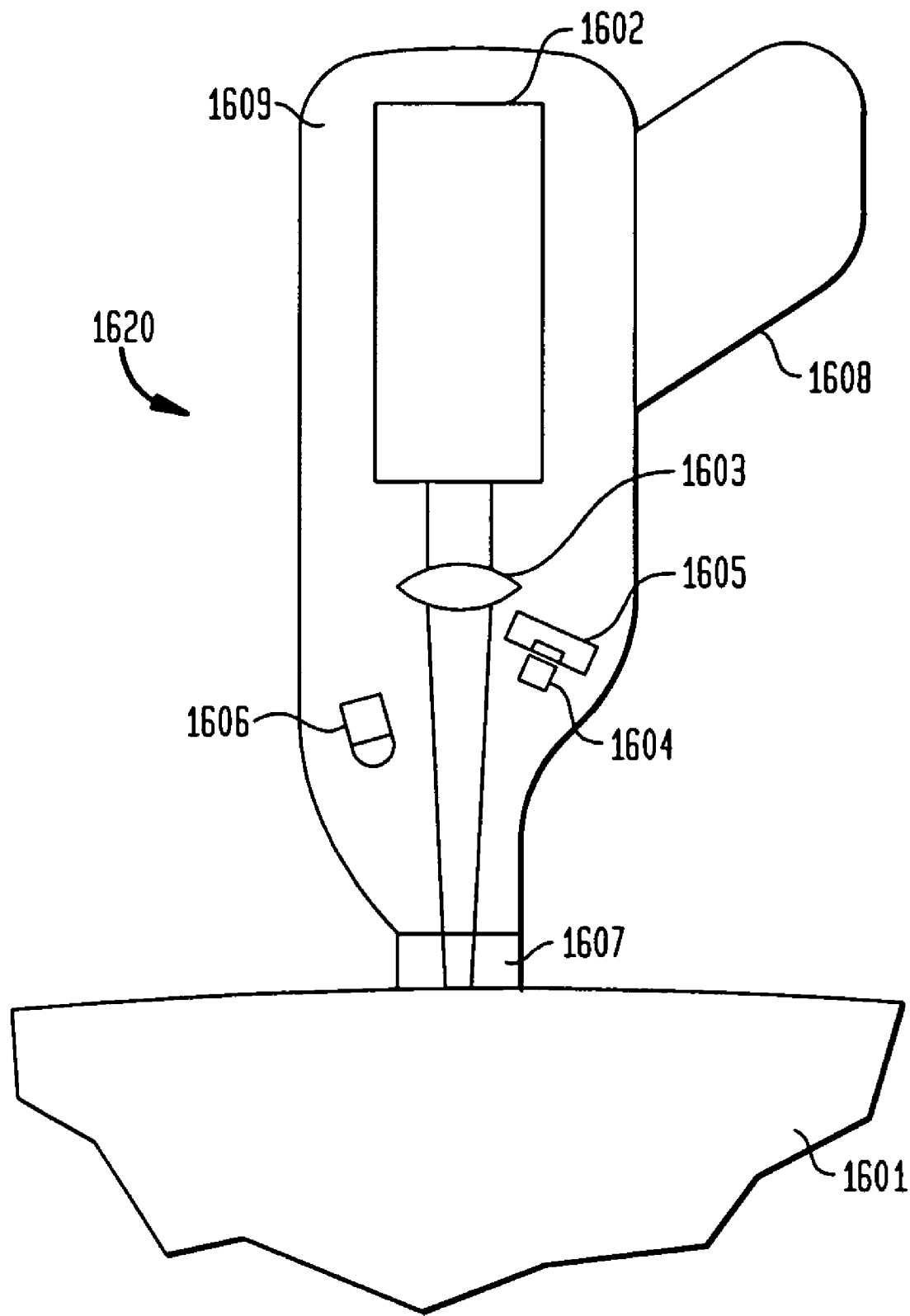
FIG. 16A is a schematic cross-sectional view of a handpiece device according to another embodiment of the invention having a therapeutic radiation source and an illumination radiation source.

FIG. 16A schematically illustrates another embodiment of a handpiece device 1620 according to the teachings of the invention that includes a housing 1609 having a head for delivering energy generated by a source 1602 disposed in the housing to a target treatment area. More particularly, a beam formation system 1603, e.g., a lens, disposed in the housing directs the energy generated by the source 1602 onto the treatment area 1601. The energy source 1602 can be, for example, a radiation source, such as a laser, a lamp or an LED. Alternatively, the energy source can be a particle source, such as dermal abrasion particle sources. An illumination source 1606, for example, an LED, illuminates the treatment area, or a selected portion thereof. At least a portion of light reflected from the treatment area, for example, in response to illumination by the source 1606, is imaged by a focusing or optical system 1604, for example, a lens, onto an image capture device 1605, e.g., a CCD camera, that generates an image of the treatment area. The image is transmitted to a display device 1608, mounted onto the housing, for viewing by a user.

The exemplary handpiece 1620 further includes a contact cooling window 1607 that thermally couples to a selected portion of the patient's skin so as to cool the patient's epidermis in the area of the skin exposed to treatment energy as the energy is deposited into a target treatment region. The cooling window 1607 is substantially transparent to both the treatment energy as well as the optical radiation generated by the light source 1602.

Figure 16B:
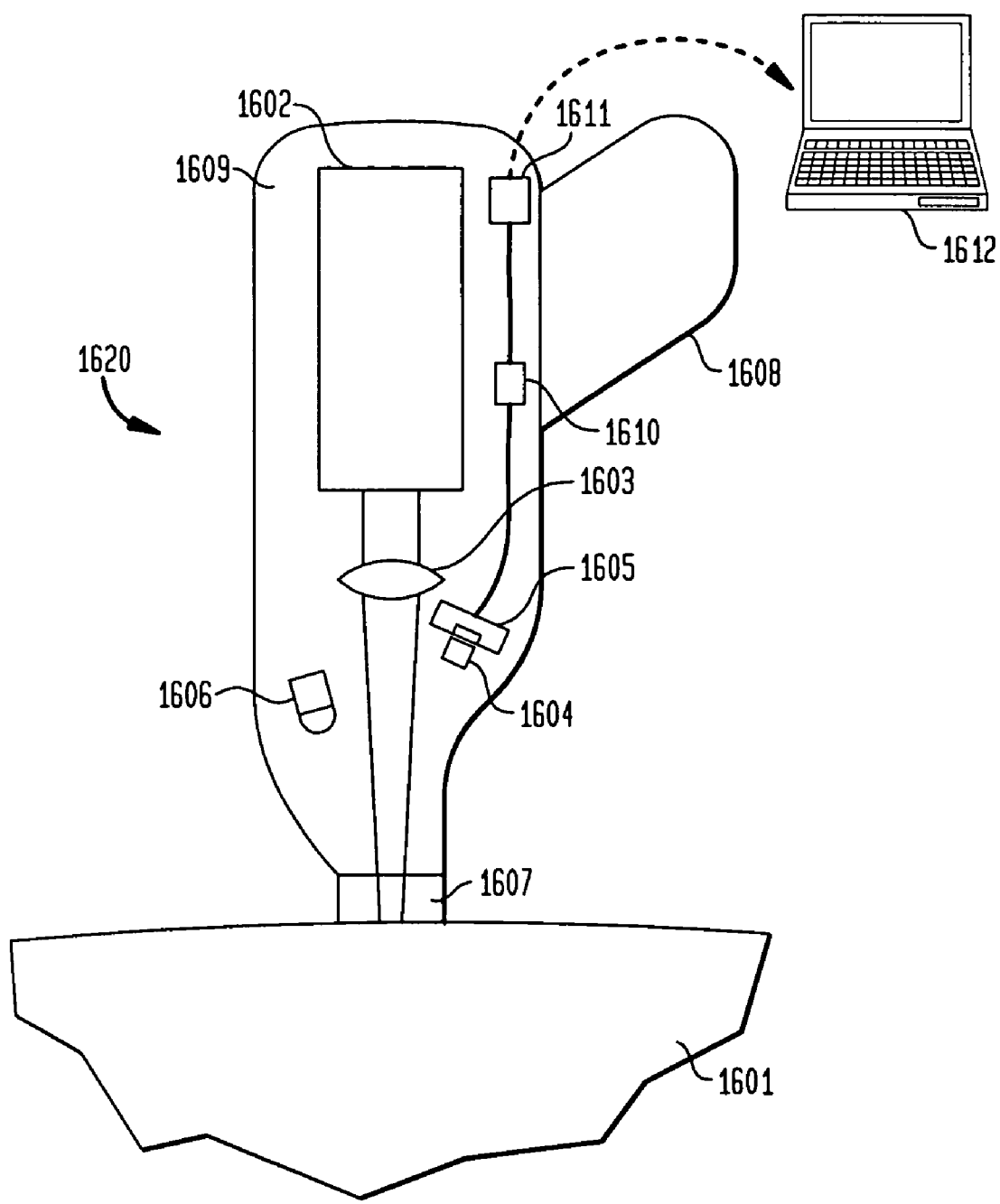
FIG. 16B is a schematic cross-sectional view of a handheld device according to one embodiment of the invention having an image capture device for generating an image of a target skin region and a memory unit for storing the images, FIG. 16C schematically depicts a handheld device according to one embodiment of the invention having a housing in which various components of the device are disposed, FIG. 16D schematically depicts a handheld device according to another embodiment of the invention, FIG. 17 schematically depicts a handheld device according to another embodiment of the invention having a source for generating therapeutic energy and a beam forming system for focusing the therapeutic energy onto a selected target skin region, and FIG. 18 schematically illustrates a handheld device according to another embodiment of the invention having a lamp source for generating treatment radiation.

FIG. 16B schematically illustrates that a memory unit 1610 can be incorporated in the handheld device 1620 for storing images obtained by the image capture device 1605. In addition, a communications interface 1611 allows the device to communicate, for example, via a wireless protocol, with an external computer. The communications interface 1611 allows for the transfer of images obtained by the image capture device 1605 to the external computer 1612, either in real time, or with a selected delay via downloading images stored by the memory unit 1610 onto the computer. Those having ordinary skill in the art will appreciate that other components, such as processors, can also be included in the device to perform desired tasks.

A variety of designs can be employed for constructing a handheld dermatological device according to the teachings of the invention, such as the device schematically depicted above in FIGS. 4A and 4B. By way of example, FIG. 16C schematically illustrates a handheld dermatological device 1620 according to another embodiment of the invention that includes a housing 1622 having an enclosure 1624 in which various components of the device, for example, a light source, such as solid state laser together with optics for delivering radiation to a treatment area, and a CCD camera 1626 for imaging the treatment area, are disposed. The enclosure includes a treatment head 1628, such as a contact tip, at a proximal end thereof for delivering treatment energy to a selected target area, for example, via a window 1630 that can also function as a cooling element. Further, a display 1632 is mounted to the enclosure at a distal end thereof that allows a user to view the images captured by the CCD camera 1626. The housing 1622 further includes a handle 1634 that allows a user, a medical professional or a home user, to hold and manually manipulate the device for delivering treatment energy to a target area.

Figure 16D:
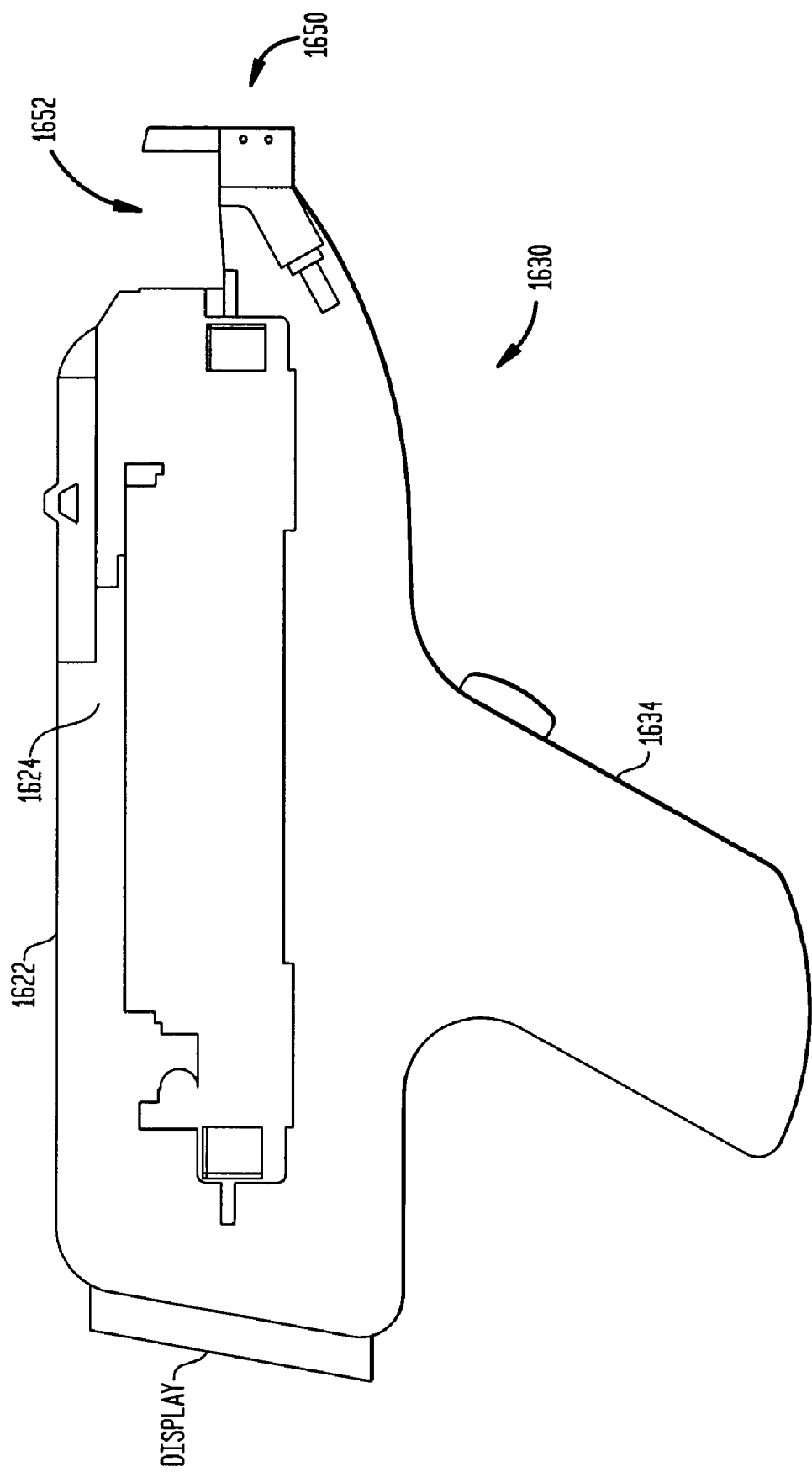

With reference to FIG. 16D, a handheld dermatological device 1630 according to another embodiment of the invention includes a housing 1622 formed of an enclosure 1624 and a handle 1634. The enclosure 1624 includes an optically transparent element 1650 mounted to a head portion thereof through which treatment radiation can be delivered to a target area. The enclosure further includes an opening 1652 that allows a user to directly view, via the transparent element 1650, a target area, albeit at a slanted viewing angle. Natural light from the sun, a cabinet lamp or a head lamp/LED projector can be used for illumination of treatment area through opening 1652 to provide natural color of the skin. In addition, a display is mounted to the housing to allow the user to view an image of the treatment area obtained by an image capture device (not shown) incorporated in the housing.

Figure 17:
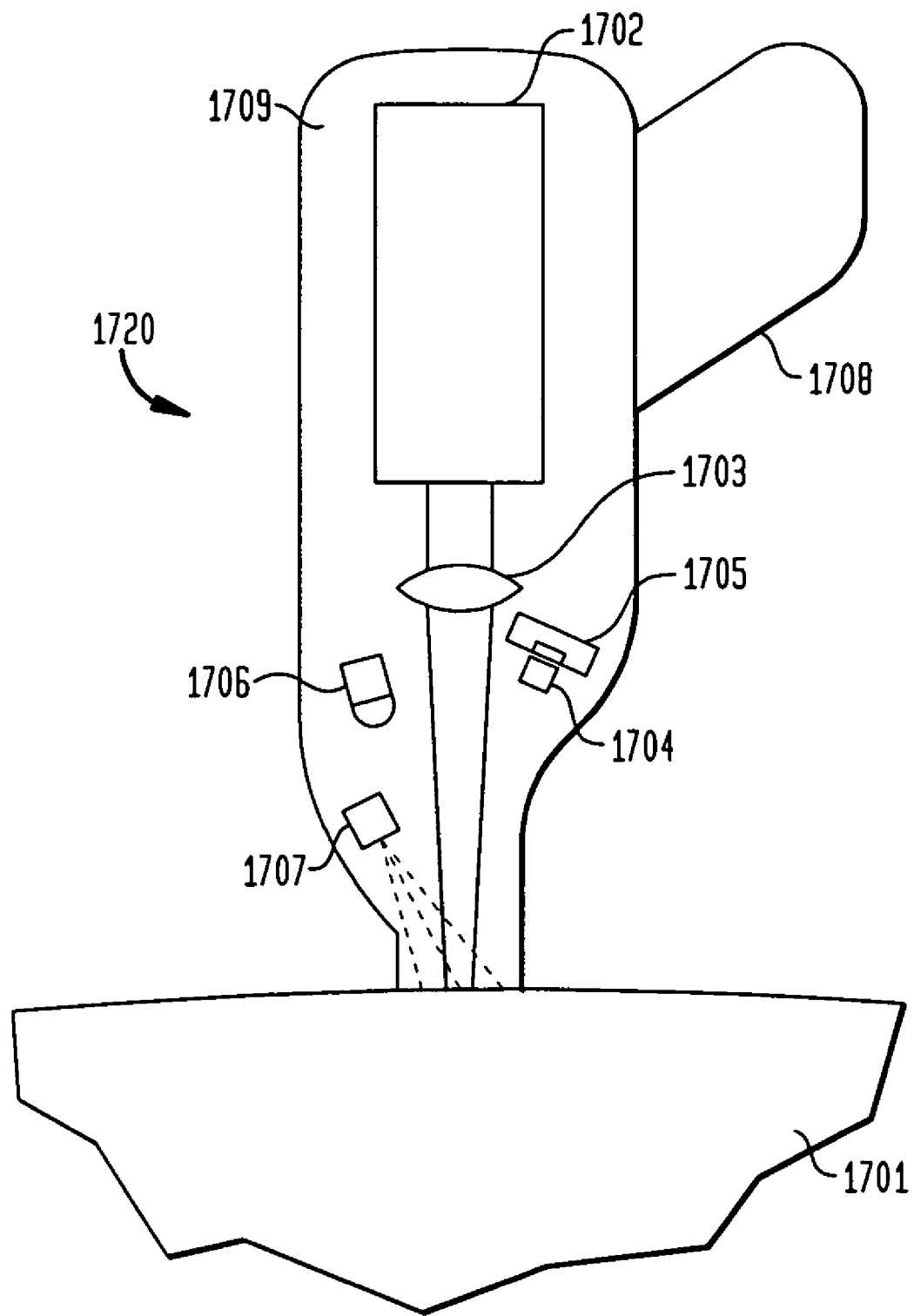

FIG. 17 schematically illustrates another embodiment of a handheld dermatological device 1720 according to the teachings of the invention that includes a source 1702 for generating therapeutic energy, e.g., electromagnetic, acoustic radiation or dermal abrasion particles, and a beam forming system 1703 for focusing the energy onto a selected target area inside a housing 1709. One or more light sources 1702 or 1706 can illuminate the target area to allow an image capture device 1705 to obtain images of this area for presentation to a viewer via a display 1708 mounted to the housing. This embodiment further includes a non-contact cooling system 1707 for cooling the target area, e.g., during application of the treatment energy. The non-contact cooling system can be, among other choices, a spray unit that sprays a suitable coolant onto the treatment area, or it can be a system for generating an air flow over the treatment area. In this case, the imaging system can also be used to control cooling of the skin by a spray, for example, by monitoring for ice formation or "lake effects," to prevent skin from over or under cooling.

Figure 18:
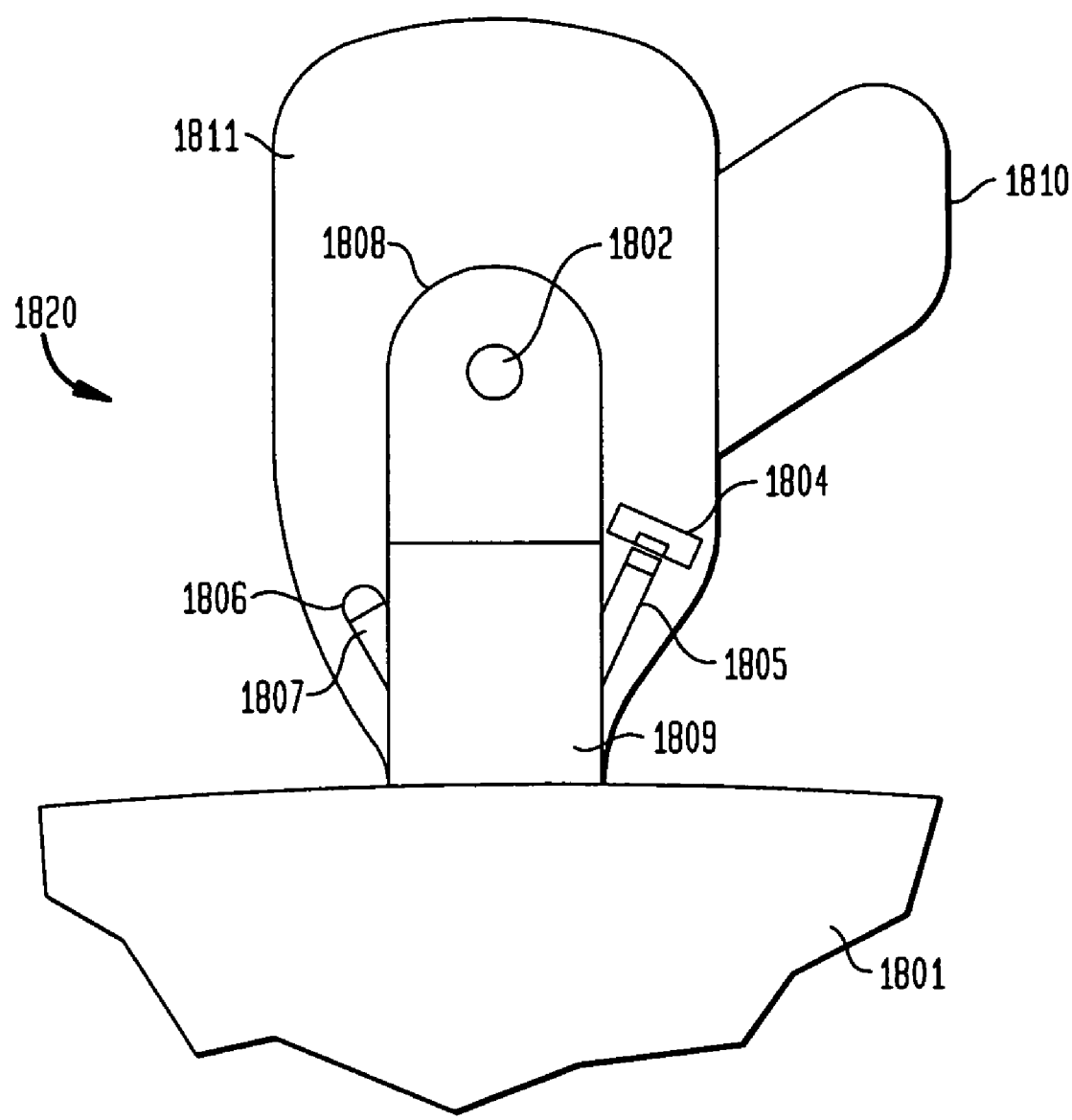

FIG. 18 schematically illustrates another handheld dermatological device 1820 according to another embodiment of the invention that includes a housing 1811 for enclosing a lamp source (e.g., arc, halogen, metal halide) or solid state lighting sources (LED) 1802 for generating radiation, e.g., broadband radiation, and a reflector 1808 that directs at least a portion of the generated radiation to a the treatment skin region or waveguide or an optically transparent window 1809 for delivery to a target treatment area. The exemplary device 1820 further includes a light source 1806, such as an LED, a laser, or a microlamp, that illuminates the target treatment area, or a portion thereof, via an optical coupling system 1807, e.g., a lens or prism. An optical coupling system 1805, e.g., a lens, focuses light reflected from the treatment area onto an image capture device 1804, e.g., a CCD camera, mounted to the device's housing for generating an image of the treatment area. The image is transmitted to a display 1810, mounted to the housing 1811, for viewing by a user. In some embodiments, one or more filters can be optically coupled to the lamp in order to select one or more wavelength bands from a broad spectrum generated by the lamp for causing desired therapeutic and/or cosmetic effects. The light from lamp 1802 can be used for illumination of the treatment area. Several lamps like 1802 can be mounted in the same reflecting chamber. Illumination sources 1806 can be mounted around skin treatment region or waveguide 1809 to provide illumination of a treatment target by banana photons. The light from illumination sources 1806 can be directly coupled to the skin. Further, a shield between 1806 and the observation skin region can be used. The depth of the illuminated area and the visualization depth into the skin can be optimized by control of incident angle of the illumination light on the 1809 contact surface, the observation angle of the optical system 1805, refractive indices of the waveguide 1809, optics 1805, 1807 and lotion, if utilized, between waveguide 1809 and the skin in a manner similar to that described above in connection with FIGS. 13A and 13B.

Those having ordinary skill in the art will appreciate that various changes can be made to the above embodiments without departing from the scope of the invention.

What is claimed is:

1. A handheld dermatological device, comprising
   a housing capable of being manually manipulated to position a head portion thereof in proximity of a person's skin surface,
   an illuminating source mounted to said housing for illuminating a target skin region,
   a solid state laser disposed in said housing for generating radiation,
   an optical system coupled to said laser for directing radiation from the laser to the target skin region,
   an image capture device mounted in said housing for generating an image of said illuminated target skin region,
   a display coupled to said housing and in communication with said image capture device to display said image, and
   a shield mounted to the head portion for shielding a portion of the skin surface through which said image capture device obtains the image of the target skin region from direct illumination by said illuminating source.

2. The device of claim 1, wherein said solid state laser comprises a rare earth doped laser.

3. The device of claim 2, wherein said solid state laser comprises a neodymium (Nd) laser.

4. The device of claim 2, wherein said solid state laser comprises a Nd:YAG laser.

5. The device of claim 1, further comprising a microprocessor in communication with said image capture device for processing one or more images obtained by said image capture device.

6. The device of claim 1, wherein said image capture device comprises a CCD camera.

7. The device of claim 1, wherein said image capture device captures at least a portion of radiation returned from the skin through said skin surface portion in response to illuminating said illuminating source.

8. A method of treating skin, comprising:
applying treatment radiation generated by a solid state laser to selected vasculature located in a target skin region,
illuminating indirectly said target skin region by radiation from at least one illumination source so as to avoid direct incidence of the radiation on at least a portion of the surface of said target skin region,
generating an image of said target skin region, and displaying said image.

9. The method of claim 8, further comprising selecting said solid state laser to be a rare earth doped laser.

10. The method of claim 8, further comprising selecting said solid state laser to be a neodymium (Nd) laser.

11. The method of claim 8, further comprising displaying said image concurrently with application of the treatment radiation.

12. The method of claim 8, further comprising utilizing said image to align a treatment radiation beam generated by said laser with said selected vasculature.

13. A handheld dermatological device, comprising
a housing through which treatment energy can be applied to a person's skin,
two illumination sources capable of generating radiation having at least two different wavelengths, said sources being mounted to a head portion of said housing for illuminating a target skin region,
a control for selectively activating said sources,
an image capture device disposed in said housing for detecting at least a portion of radiation scattered by said target skin region in response to illumination by at least one of said sources, and
a shield positioned in proximity of at least one of said illumination sources for shielding a selected skin surface segment from direct illumination by said source.

14. The device of claim 13, wherein said control is adapted for activating said sources in different temporal intervals.

15. The device of claim 13, wherein said control is adapted for triggering said image capture device to form an image of the target region upon activation of at least one of said sources.

16. The device of claim 13, wherein said image capture device is adapted to collect radiation via said shielded skin surface segment radiation scattered by said target skin region.

17. The device of claim 13, further comprising a treatment source disposed in said housing for applying treatment energy to said target skin region through said shielded skin surface segment.

18. The device of claim 13, wherein said control is adapted to activate said illumination sources in accordance to a preset temporal pattern.

* * * * *